(12) United States Patent
Hara et al.

(10) Patent No.: US 10,995,178 B2
(45) Date of Patent: May 4, 2021

(54) ALKYLOXIRANE DERIVATIVE, COSMETIC MATERIAL FOR HAIR, HYDRAULIC OIL COMPOSITION, RESIN COMPOSITION CURABLE BY ACTINIC RAYS, AND OIL CLEANSING AGENT

(71) Applicant: NOF CORPORATION, Tokyo (JP)

(72) Inventors: Yusuke Hara, Kanagawa (JP); Kazuaki Wakita, Kanagawa (JP); Mitsushi Kusumoto, Kanagawa (JP); Megumi Nagayama, Amagasaki (JP); Shunsuke Monjiyama, Amagasaki (JP); Aiko Yamanaka, Amagasaki (JP); Hideki Kawamoto, Amagasaki (JP)

(73) Assignee: NOF CORPORATION, Tokyo (JP)

( * ) Notice: Subject to any disclaimer, the term of this patent is extended or adjusted under 35 U.S.C. 154(b) by 37 days.

(21) Appl. No.: 16/324,229

(22) PCT Filed: Aug. 4, 2017

(86) PCT No.: PCT/JP2017/028362
§ 371 (c)(1),
(2) Date: Feb. 8, 2019

(87) PCT Pub. No.: WO2018/030283
PCT Pub. Date: Feb. 15, 2018

(65) Prior Publication Data
US 2020/0190260 A1     Jun. 18, 2020

(30) Foreign Application Priority Data

Aug. 10, 2016  (JP) .............................. JP2016-157659
Dec. 26, 2016  (JP) .............................. JP2016-250917
Jul. 11, 2017   (JP) .............................. JP2017-135177

(51) Int. Cl.
*C08G 65/08* (2006.01)
*A61K 8/86* (2006.01)
(Continued)

(52) U.S. Cl.
CPC ................ *C08G 65/08* (2013.01); *A61K 8/86* (2013.01); *A61Q 5/12* (2013.01); *C08G 18/48* (2013.01);
(Continued)

(58) Field of Classification Search
CPC .... C08G 65/08; C08G 65/2663; C08G 18/48; A61K 8/86; A61Q 1/14; A61Q 5/12;
(Continued)

(56) References Cited

U.S. PATENT DOCUMENTS 5,470,813 A   11/1995   Le-Khac
5,731,407 A   3/1998    Le-Khac
(Continued)

FOREIGN PATENT DOCUMENTS

CN    1407001 A     4/2003
CN    103756764 A   4/2014
(Continued)

OTHER PUBLICATIONS

Extended European Search Report dated Jan. 31, 2020 in European Application No. 17839354.2.
(Continued)

*Primary Examiner* — James C Goloboy
(74) *Attorney, Agent, or Firm* — Sughrue Mion, PLLC

(57) ABSTRACT

An alkyloxirane derivative represented by formula (1), wherein $M_H$ and $M_L$ calculated from a gel permeation chromatogram satisfy formula (2):

$$Z\text{—}[O\text{-}(AO)n\text{-}H]x \quad (1)$$

(Continued)

Elution time where Z represents a residual group of a compound having 1 to 22 carbon atoms and one to six hydroxyl groups and wherein all of the hydroxyl groups are excluded from said compound; x is 1 to 6; and AO represents an oxyalkylene group having 3 carbon atoms; and n is 25 or more;

$$0.35 \leq M_L/M_H \leq 0.75 \quad (2)$$

where $M_H$ represents a distance between point O and intersecting point P, and $M_L$ represents a distance between point Q and intersecting point P determined from the chromatogram.

7 Claims, 4 Drawing Sheets

(51) Int. Cl.
*A61Q 5/12* (2006.01)
*C08G 18/48* (2006.01)
*C10M 105/38* (2006.01)
*C10M 145/36* (2006.01)
*C10M 169/04* (2006.01)
*C11D 3/37* (2006.01)

(52) U.S. Cl.
CPC ........ *C10M 105/38* (2013.01); *C10M 145/36* (2013.01); *C10M 169/04* (2013.01); *C11D 3/3707* (2013.01); *C10M 2207/28* (2013.01); *C10M 2209/104* (2013.01)

(58) Field of Classification Search
CPC .............. C10M 105/38; C10M 145/36; C10M 169/04; C10M 2207/28; C10M 2209/104; C11D 3/3707
See application file for complete search history.

(56) References Cited

U.S. PATENT DOCUMENTS

| | | | | |
|---|---|---|---|---|
| 6,627,576 | B2* | 9/2003 | Sugiyama | B01J 27/26 502/175 |
| 2007/0286837 | A1* | 12/2007 | Torgerson | A61K 8/898 424/70.122 |
| 2012/0172537 | A1 | 7/2012 | Arai et al. | |
| 2014/0275313 | A1* | 9/2014 | Brown | C08G 65/2663 521/174 |
| 2014/0308015 | A1* | 10/2014 | Bookbinder | G02B 6/0283 385/124 |
| 2017/0121625 | A1* | 5/2017 | Qian | C10M 133/44 |
| 2018/0079982 | A1 | 3/2018 | Kaneko et al. | |

FOREIGN PATENT DOCUMENTS

| | | |
|---|---|---|
| EP | 1 288 244 A1 | 3/2003 |
| JP | 07-196778 A | 8/1995 |
| JP | 10-007787 A | 1/1998 |
| JP | 2002-338628 A | 11/2002 |
| JP | 2004-269776 A | 9/2004 |
| JP | 2005-104892 A | 4/2005 |
| JP | 2006-328364 A | 12/2006 |
| JP | 2009-084229 A | 4/2009 |
| JP | 2009-196375 A | 9/2009 |
| JP | 2013-189423 A | 9/2013 |
| JP | 2016-014091 A | 1/2016 |
| JP | 2016-045349 A | 4/2016 |
| JP | 2016-185932 A | 10/2016 |
| JP | 2016-190892 A | 11/2016 |
| WO | 99/48607 A1 | 9/1999 |
| WO | 01/90218 A1 | 11/2001 |
| WO | 03/008482 A1 | 1/2003 |
| WO | 2011/034030 A1 | 3/2011 |

OTHER PUBLICATIONS

R. A. Livigni et al., "Poly(Propylene Ether) Polyols Prepared With a Zinc Hexacyanocobaltate Complex Catalyst," ACS Symposium Series, 1975, pp. 20-37 (19 pages), vol. 6.

Yi-Jun Huang et al., "Controlled Ring-Opening Polymerization of Propylene Oxide Catalyzed by Double Metal-Cyanide Complex," Journal of Polymer Science: Part A: Polymer Chemistry, 2002, pp. 1142-1150, vol. 40.

International Search Report of PCT/JP2017/028362 dated Oct. 10, 2017.

Office Action dated Sep. 28, 2020 issued from the State Intellectual Property Office of P. R. China in Chinese Application No. 201780047198.0.

* cited by examiner

ALKYLOXIRANE DERIVATIVE, COSMETIC MATERIAL FOR HAIR, HYDRAULIC OIL COMPOSITION, RESIN COMPOSITION CURABLE BY ACTINIC RAYS, AND OIL CLEANSING AGENT

CROSS REFERENCE TO RELATED APPLICATIONS

This application is a National Stage of International Application No. PCT/JP2017/028362 filed Aug. 4, 2017, claiming priority based on Japanese Patent Application No. 2016-157659 filed Aug. 10, 2016, Japanese Patent Application No. 2016-250917 filed Dec. 26, 2016, and Japanese Patent Application No. 2017-135177 filed Jul. 11, 2017.

TECHNICAL FIELD

The present invention is related to a novel alkyloxirane derivative effectively used in various kinds of applications such as a hair cosmetic, hydraulic oil composition, an active energy ray-curable composition, an oil cleansing agent or the like.

BACKGROUND ARTS

Generally, an alkyloxirane derivative is synthesized by anion polymerization of ring-opening addition of an alkyloxirane, such as oxirane, methyl oxirane and ethyl oxirane, to an initiating agent having an active hydrogen such as an alcohol using an alkali metal hydroxide such as potassium hydroxide. In particular, in the case that methyloxirane is used in the anion-polymerization to synthesize a methyloxirane derivative, an unsaturated mono-ol is generated as a byproduct, whose amount of production is increased as an increase of the molecular weight of the methyloxirane derivative. As a result, an increase of the molecular weight of the methyloxirane derivative is interrupted and the ratio of the derivatives of lower molecular weights is increased in the molecular weight distribution, which is problematic.

For solving the problem, it has been used a phosphazene compound or the like having P=N bond, a catalyst of a complex of a composite metal cyanide or the like. By using such catalyst, it is possible to reduce the generation of the unsaturated mono-ol and to synthesize the methyloxirane derivative of a high molecular weight. Among the catalysts, the catalyst of the complex of the composite metal cyanide has higher catalyst activity than the former catalyst, and thus useful polymerizing catalyst for producing the methyloxirane derivative (Non-patent document 1).

It is further reported that the high-molecular methyloxirane derivative synthesized by using the catalyst of the complex of the composite metal cyanide has a lower content of the unsaturated mono-ol and narrower distribution of the molecular weights. As the molecular distribution of the methyloxirane derivative is narrower, the viscosity is lower and thus easy to handle, so that it is considered to be useful raw material of polyurethane. It is reported that the method of producing methyloxirane derivative having the narrower distribution of molecular weight (Patent documents 1, 2 and 3).

However, in applications of a lubricant oil or the like, there is a problem that the viscosity is not high enough. Further, most of the number (number of the functional groups) of hydroxyl groups in the molecule of such methyloxirane derivative of a high molecular weight is 2 or more, and it is particularly difficult to synthesize a high-molecular weight methyloxirane derivative having a single functional group.

The alkyloxirane derivative has been used as a material for a cosmetic. For example, patent document 4 discloses a hair cosmetic blending polyoxypropylene butyl ether. It is described that the cosmetic can be washed by rinse to obtain smooth finishing sense in hairs. However, in the case that such hair cosmetics is used, hairs are got loose by water and can be easily passed by fingers while hairs are rinsed with a large amount of water.

However, creaking occurs during the removal of water from hairs and stiff feel or sticky feel may be left in hairs after the rinsing, which are problematic.

RELATED TECHNICAL DOCUMENTS

Non-Patent Documents (Non-Patent Document 1)
ACS Symposium Series, Vol. 6, pp 20-37 (1975)

Patent Documents (Patent document 1) Japanese Patent publication No. 1998-007787A
(Patent document 2) Japanese Patent publication No. 2004-269776A
(Patent document 3) WO2011/034030 A1
(Patent document 4) Japanese Patent publication No. 2013-189423A
(Patent document 5) Japanese Patent publication No. 2016-190892A
(Patent document 6) Japanese Patent publication No. 2016-014091A
(Patent document 7) Japanese Patent publication No. 2002-338628A
(Patent document 8) Japanese Patent publication No. 2006-328364A
(Patent document 9) Japanese Patent publication No. 2009-196375A
(Patent document 10) Japanese Patent publication No. 2016-045349A
(Patent document 11) Japanese Patent publication No. 2009-084229A
(Patent document 12) Japanese Patent publication No. 2005-104892A
(Patent document 13) Japanese Patent publication No. 2016-185932A

SUMMARY OF THE INVENTION

Object to be Solved by the Invention

Patent document 6 described a hydraulic oil composition having high compatibility with a sealing material. However, its ester content is low, so that the essential characteristics of the blended ester are deteriorated.

Further, a hydraulic oil belongs to a lubricant oil used under a high pressure. In the case that the lubricating property (wear resistance) is insufficient, wear of sliding parts may occur. It is thus required consideration of lubricating property (wear resistance).

However, although each of compositions containing urethane (meth)acrylate described in patent documents 7 to 9 provided high cross-linking density and high surface hardness, brittleness may be provided to deteriorate the resistance against impact, which is problematic. Further, although a resin composition described in patent document 10 provides a hardened product having high surface hardness and scratch-resistant property, the resistance against impact of a thin film of the hardened product is not sufficiently high.

Further, it has been not attained to provide cleansing ability, rinsing property and moist feeling of skin after washing, as well as elongation and slippery feel in the case of applying with a make-up to reduce damages on the skin.

An object of the present invention is to provide an alkyloxirane derivative of a high molecular weight suitable in various kinds of applications such as a hair cosmetic, hydraulic oil composition, an active energy ray-curable composition and an oil cleansing agent.

Further, an object of the present invention is to provide a novel alkyloxirane derivative in which sticky feel or stiff feel is not left and is excellent in slippery feel during removal of water from hairs after the rinse of the hairs in a hair cosmetic with the derivative blended therein.

Another object of the present invention is to provide a hydraulic oil composition excellent in compatibility with a sealant and lubricating property (wear resistance).

Still another object of the present invention is to provide an active energy ray-curable resin composition capable of providing a cured product excellent in properties, specifically transparency, surface hardness and resistance against impact, required for a substrate of a display device or the like.

Still another object of the present invention is to provide an oil cleansing agent having good cleansing ability, rinsing property during washing, initial elongation in application, and slippery feel in use, and capable of providing moist feeling on skin after washing to reduce damages on the skin.

Solution for the Object

The inventors intensively studied the problems as described above and found that it can be obtained a novel alkyloxirane derivative suitable for various kinds of applications and whose molecular weight pattern obtained by gel permeation chromatography is not symmetrical in right and left sides and is biased toward the side of higher molecular weight. It is then found that, by blending the derivative in a hair cosmetic for example, it can be obtained the hair cosmetic with sticky feel or stiff feel not left and excellent in slippery feel during removal of water from hairs after the rinse of the hairs.

That is, the present invention is as follows.

(1) An alkyloxirane derivative represented by formula (1) below, wherein $M_H$ and $M_L$ calculated from a chromatograph obtained by gel permeation chromatography measurement of said alkyloxirane derivative satisfy formula (2) below.

$$Z\text{—}[O\text{-}(AO)n\text{-}H]x \tag{1}$$

(In the formula (1),

Z represents a residual group of a compound having a carbon number of 1 to 22 and one to six hydroxyl groups wherein all of said hydroxyl groups are excluded from said compound, x represents a number of 1 to 6, AO represents an oxyalkylene group having a carbon number of 3, and n represents a number of 25 or more.)

$$0.35 \leq M_L/M_H \leq 0.75 \tag{2}$$

(Provided that L is assigned to a length of a perpendicular line from the maximum point K at which an intensity of a refractive index on said chromatogram takes the maximum value to a base line B, provided that points O and Q are assigned to two points at which said intensity of said refractive index on said chromatogram is L/2, said point O has a shorter elution time and said point Q has a longer elution time, and provided that P is an intersecting point where a straight line G connecting said point O and point Q intersects the perpendicular line from said maximum point K to said base line, $M_H$ represents a distance between said point O and said intersecting point P, and $M_L$ represents a distance between said point Q and said intersecting point P.)

(2) The alkyloxirane derivative of (1), wherein As calculated from said chromatogram satisfies the following formulas (3) and (4).

$$As = W_{1/2}/W_{5\%} \tag{3}$$

$$0.30 \leq As \leq 0.70 \tag{4}$$

(Provided that points S and R are assigned to two points at which said intensity of said refractive index on said chromatogram is L/20, said point R has a shorter elution time and said point S has a longer elution time, and provided that T is assigned to an intersecting point where a straight line H connecting said point R and point S intersects said perpendicular line from said maximum point K to said base line B, $W_{1/2}$ is assigned to a distance between said point R and said intersecting point T, and $W_{5\%}$ is assigned to a distance between said point R and said point S.)

(3) The alkyloxirane derivative of (1) or (2), wherein said alkyloxirane derivative is represented by the following formula (5).

$$R^1O\text{-}(AO)n\text{-}H \tag{5}$$

(In the formula (5), $R^1$ represents a hydrocarbon group having a carbon number of 1 to 22;

AO represents said oxyalkylene group having a carbon number of 3: and n represents said number of 25 or more.)

(4) A hair cosmetics comprising said alkyloxirane derivative of any of (1) to (3).

(5) A hydraulic oil composition comprising:

an ester compound (A) as follows; and said alkyloxirane derivative (B) of any one of (1) to (3).

wherein 1.0 to 30.0 mass parts of said alkyloxiran derivative (B) is contained with respect to 100 mass parts of said ester compound (A).

(A) said ester compound of neopentyl polyol having a carbon number of 5 to 10 and an alcohol valence of 3 to 6 and of a fatty acid having a carbon number of 6 to 22

(6) An active energy ray-curable resin composition comprising the following component (A) and component (B). wherein a ratio of a mass of said component (A) with respect to a mass of said component (B) ((A)/(B)) is 1/99 to 30/70.

said component (A):

an urethane compound of a reaction product of said alkyloxirane compound (a1) of any one of (1) to (3) and of an isocyanate (a2) comprising two or more isocyanate groups in a molecule of said isocyanate said component (B):
an urethane (meth)acrylate compound having two or more ethylenically unsaturated groups
(7) An oil cleansing agent comprising:
1 to 20 mass % of a component (a) below;
45 to 90 mass % of a component (b) below; and
5 to 50 mass % of a component (c) below.
(a) said alkyloxirane compound of (2) or (3)
(b) a liquid oily component
(c) a surfactant of an ester of a polyvalent alcohol and a fatty acid Effects of the Invention According to the present invention, it is possible to provide a novel alkyloxirane derivative suitable for various kinds of applications and whose distribution of molecular weight is biased toward the side of higher molecular weight. In the case that the derivative is blended in a hair cosmetic, for example, sticky feel or stiff feel is not left and the cosmetic is particularly excellent in slippery feel in removing water from hairs after rinsing.

The hydraulic oil composition of the present invention is excellent in compatibility with a sealant and lubricating property (wear resistance).

The active energy ray-curable resin composition of the present invention is capable of providing a cured product excellent in transparency, surface hardness and resistance against impact.

The oil cleansing agent of the present invention has good cleansing effect and rinsing property during washing, is excellent in elongation in the initial application and slippery feel in use, and provides moisture feel on skin after washing to reduce damages on the skin.

MODES FOR CARRYING OUT THE INVENTION

Figure 1:
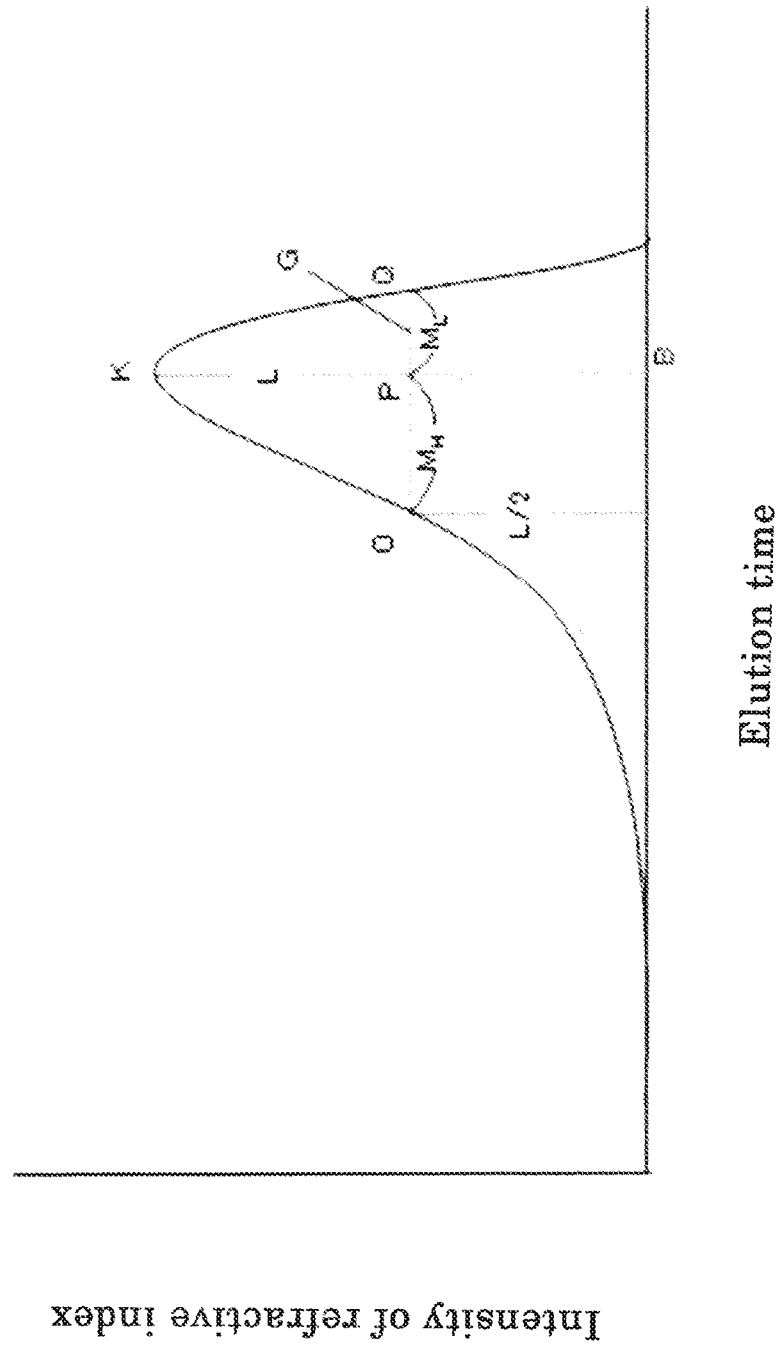
FIG. 1 is a model chromatogram for illustrating $M_L$ and $M_H$ defined in the present invention.

In the specification, a numeral value range defined by using (~) is to include numerical values at both ends (upper end and lower end) of (~). For example, (2~5) means 2 or higher and 5 or lower.
(Alkyloxirane Derivative)
The alkyloxirane derivative of the present invention is a compound represented by the formula (1).

Z—[O-(AO)$n$-H]$x$ (1)

In the formula (1), Z represents a residual group of a compound having a carbon number of 1 to 22 and hydroxyl group(s) of 1 to 6 excluding all the hydroxyl group(s). x represents a number of 1 to 6, AO represent an oxyalkylene group having a carbon number of 3, and n represent an average addition molar number of the oxyalkylene group AO and 25 or higher.

In the formula (1), Z represents a residual group of the compound Z (OH) x having a carbon number of 1 to 22 and 1 to 6 hydroxyl group(s) excluding all the hydroxyl group(s) (OH). x represent a number of the hydroxyl groups in the compound. Z is the residual group of the compound having 1 to 6 hydroxyl group (s) and a carbon number of 1 to 22, preferably a carbon number of 1 to 14 and more preferably a carbon number of 1 to 6, excluding all the hydroxyl groups. x represent a number of the hydroxyl groups contained in the compound of Z and 1 to 6.

The compound having 1 to 6 hydroxyl group(s) includes methanol, ethanol and butanol in the case x is 1, ethylene glycol, propylene glycol and hexylene glycol in the case that x is 2, glycerin and trimethylolpropane in the case that x is 3, erythritol, pentaerythritol, sorbitan, diglycerin and alkyl glycoside in the case that x is 4, xylitol in the case that x is 5, dipetaerythritol, sorbitol, inositol and the like in the case that x is 6. Further, as the compound having 1 to 6 hydroxyl group(s), the mixtures of the compounds may be used. X is preferably 1 to 3 and more preferably 1 or 2.

In the formula (1), Z may be R$^1$O and in this case, x may be 1 or x may be 2 to 6. In this case, R is a hydrocarbon group having a carbon number of 1 to 22.

The hydrocarbon group having a carbon number of 1 to 22 represented by R$^1$ is a functional group composed of carbon and hydrogen atoms. The hydrocarbon group may be one selected from alkyl group, alkenyl group, cycloalkyl group, aryl group or aralkyl group, may preferably be alkyl group or alkenyl group, more preferably be alkyl group or alkenyl group each having a carbon number of 1 to 14, more preferably be alkyl group or alkenyl group each having a carbon number of 1 to 6, and most preferably be alkyl group having a carbon number of 1 to 6. The alkyl group having a carbon number of 1 to 6 may be of straight chain or branched chain, and straight chain alkyl group is more preferred. The straight chain alkyl group having a carbon number of 1 to 6 includes methyl group, ethyl group, propyl group, butyl group, hexyl group and the like, for example. The hydrocarbon group having a carbon number of 1 to 22 represented by R may be single kind or two or more kinds.

AO represents an oxyalkylene group having a carbon number of 3. Further, n represents an average addition molar number and 25 or more. In the case that n is less than 25, the viscosity is low, and in the case that it is blended in the hair cosmetic, the slippery feel during the removal of water from hairs after the rinsing may become insufficient. On the viewpoint, n is 25 or more and more preferably 50 or more.

Further, as n is larger, the viscosity is increased. On the viewpoint of ease of blending, n may preferably be 150 or less and more preferably be 120 or less.
(GPC Characteristic of Alkyloxirane Derivative)
The alkyloxirane derivative of the present invention is defined by chromatogram obtained by using a differential diffractometer in gel permeation chromatography (GPC). The chromatogram is a graph showing relationship between the intensity of refractive index and elution time. According to the alkyloxirane derivative of the present invention, the chromatogram is unsymmetrical in the right and left sides and satisfies the formula (2). Here, as $M_L/M_H$ is nearer to 1, the pattern of the chromatogram is more symmetrical in the right and left sides.

$$0.35 \leq M_L/M_H \leq 0.75 \quad (2)$$

Here, FIG. 1 is a model chromatogram obtained by gel permeation chromatography of an alkyloxirane derivative. The horizontal axis indicates the elution time and vertical axis indicates the intensity of refractive index obtained by using the differential diffractometer.

In the case that a sample solution is injected into and developed in a gel permeation chromatograph, the elution of molecules having the highest molecular weight is initiated first, and the elution curve is raised as an increase of the intensity of the refractive index. Thereafter, the elution curve goes down from the maximum point K where the intensity of the refractive index takes the maximum value.

Further, in the case that there is a plurality of maximum points of the intensity of the refractive index of the chromatogram in the gel permeation chromatography of the inventive alkyloxirane derivative, the maximum point K is defined where the intensity of the refractive index is the highest among them. Further, in the case that there is a plurality of the maximum points having the same intensity of the refractive index, the maximum point K is defined as that having a longer elution time. Further, peaks derived from a developing solvent used for the gel permeation chromatography and peaks derived from deviation of the base line due to a column or system used are excluded.

$M_L/M_H$ is calculated from the chromatogram as described below.

(1) A perpendicular line is drawn from the maximum point K of the intensity of refractive index to the base line B on the chromatogram and L is assigned to a length of the perpendicular line.

(2) Among two points where the intensity of the refractive index is L/2 in the chromatogram, O is assigned to the point having a shorter elution time and Q is assigned to the point having a longer elution time.

(3) P is assigned to an intersecting point of a straight line connecting the point O and point Q and of the perpendicular line drawn from the maximum point K of the intensity of the refractive index to the base line B.

(4) $M_H$ is assigned to a distance between the point O and point Q, and $M_L$ is assigned to a distance between the intersecting point P and the point Q.

The alkyloxirane derivative of the present invention satisfies $0.35 \leq M_L/M_H \leq 0.75$. In the case that $M_L/M_H$ exceeds 0.75, the viscosity of the alkyloxirane derivative is lowered. For example, in the case that it is blended in a hair cosmetic, the slippery feel during the removal of water from hairs is not obtained after the rinsing. On the viewpoint, $M_L/M_H$ is made 0.75 or lower and preferably 0.62 or lower.

Further, as $M_L/M_H$ becomes lower, the bias of the molecular weight distribution on the side of the higher molecular weight is large, so that an increase of the viscosity due to the bias is observed. In the case that $M_L/M_H$ is less than 0.35, the viscosity becomes too high, so that it becomes difficult to blend it into a cosmetics. In the viewpoint, $M_L/M_H$ is 0.35 or higher and more preferably be 0.36 or higher.

According to a preferred embodiment, in the gel permeation chromatography, the chromatogram represented by the intensity of refractive index obtained by a differential refractometer and elution time is unsymmetrical in the right and left sides, and an unsymmetrical value As of peaks of the chromatogram calculated as follows satisfies the following formulas (3) and (4).

$$As = W_{1/2}/W_{5\%} \quad (3)$$

$$0.30 \leq As \leq 0.70 \quad (4)$$

Figure 2:
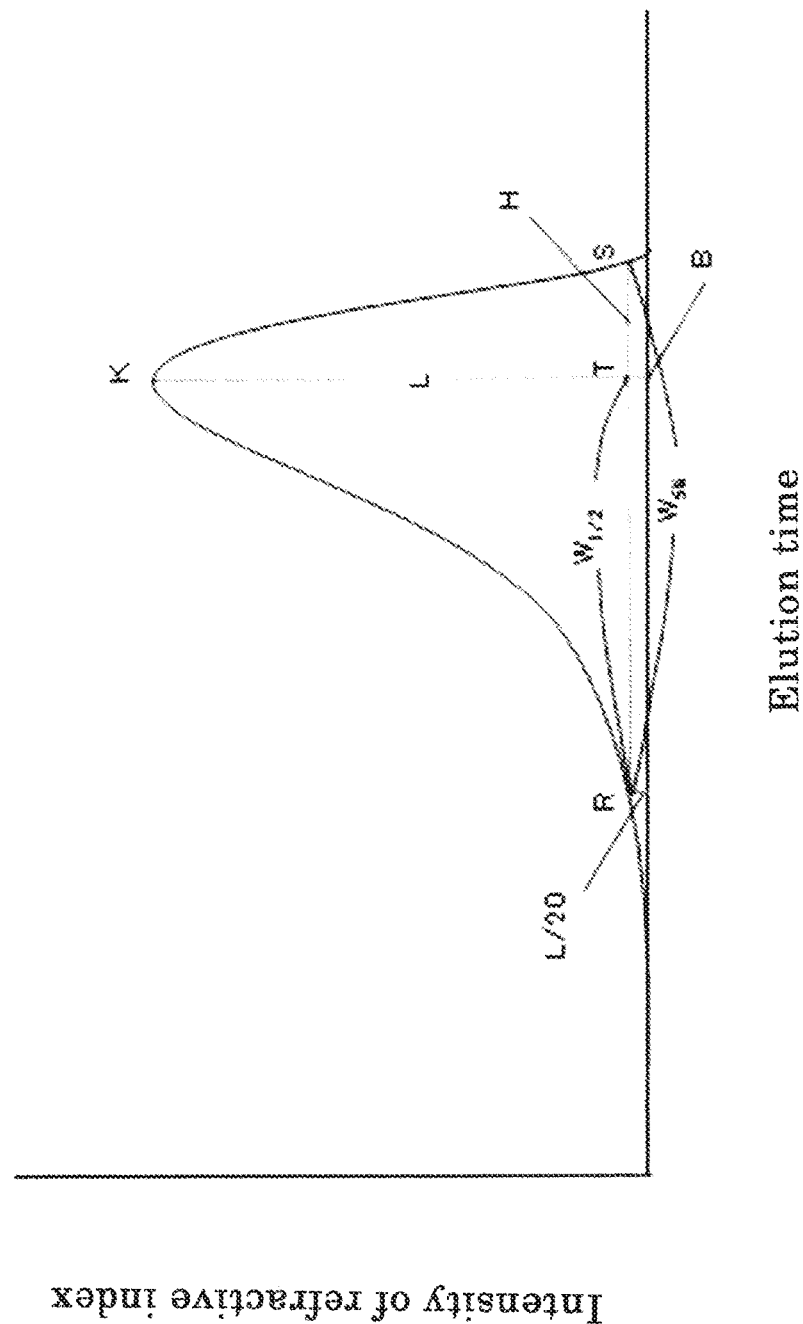
FIG. 2 is a model chromatogram for illustrating $W_{1/2}$ and $W_{5\%}$ defined in the present invention.

It will be further described the method of calculating As referring to the model chromatogram shown in FIG. 2. The horizontal axis indicates the elution time and the vertical axis indicates the intensity of refractive index obtained by using a differential refractometer.

In the case that a sample solution is injected into and developed in a gel permeation chromatograph, the elution of molecules having the highest molecular weight is initiated first, and the elution curve is raised as an increase of the intensity of the refractive index. Thereafter, the elution curve goes down from the maximum point K where the intensity of the refractive index takes the maximum value.

(1) L is a length of the perpendicular line drawn from the maximum point K of the intensity of the refractive index on the chromatogram to the base line B.

(2) Among two points where the intensity of the refractive index is L/20 on the chromatogram, R is assigned to the point having a shorter elution time and S is assigned to a longer elution time.

(3) T is assigned to an intersecting point of a straight line H connecting the point R and point S and the perpendicular line drawn from the maximum point K of the intensity of the refractive index to the base line B.

(4) $W_{1/2}$ is assigned to a distance between the point R and intersecting point T, and $W_{5\%}$ is assigned to a distance between the point R and point S.

According to a preferred embodiment, $0.305 \leq As \leq 0.70$ is satisfied. By making As 0.70 or lower, the viscosity is improved and, in the case that the alkyloxirane derivative is blended in the hair cosmetic, for example, slippery feel during the removal of water from hairs after the rinsing is promoted. On the viewpoint, As may more preferably be 0.65 or lower.

Further, as As is lower, the bias of the distribution of the molecular weight on the higher molecular weight side is made larger, so that an increase of the viscosity due to this is observed. By making As 0.30 or higher, it is possible to suppress the increase of the viscosity so that the blending into a cosmetic can be made easier. On the viewpoint, As may more preferably be 0.57 or higher.

According to the present invention, the gel permeation chromatography (GPC) for obtaining $M_L$, $M_H$ and As is performed as follows. As the system, a GPC101GPC dedicated system "SHODEX" (Trade mark), "SHODEX RI-71s" as the differential refractometer, and "SHODEX KF-G" is used as a guard column. Three columns of "HODEX KF804L" are continuously equipped as the columns, the temperature of the columns is made 40° C., tetrahydrofuran is flown at a flowing rate of 1 ml/minute as a developing solvent, 0.1 ml of tetrahydrofuran solution of the thus obtained reaction product of a content of 0.1 mass percent is injected and "BORWIN GPC calculation program" is used to obtain the chromatogram represented by the intensity of the refractive index and elution time.

In the case that the alkyloxirane derivative of the present invention is produced, preferably, alkylene oxide having a carbon number of 3, that is, methyloxirane is subjected to ring-opening addition under the presence of a complex metal cyanide catalyst (referred to as DMC catalyst below) as an initiator. In a reaction container, an initiator having at least one hydroxyl group in the molecule and the DMC catalyst are charged, and methyloxirane is continuously or intermittently added under an inert gas atmosphere upon stirring to perform the addition polymerization. Methyloxirane may be added under pressure or under ambient pressure.

At this time, although an average supply rate of methyloxirane is not limited, it may be preferably be changed depending on a charged amount of methyloxirane. Specifically, provided that $V_1$ is assigned to a rate (supply amount per an unit time) during the supply of 5 to 20 wt % of a total supply amount of methyloxirane, that $V_2$ is assigned to a rate during the supply of 20 to 50 wt % of a total supply amount of methyloxirane, and that $V_3$ is assigned to a rate during the supply of 50 to 100 wt % of the total supply amount of methyloxirane, it is preferred to adjust the average supply rates of methyloxirane satisfying $V_1/V_2=1.1$ to 2.0 and $V_2/V_3=1.1\sim1.5$.

Further, the reaction temperature may preferably be made 50 to 150° C. and more preferably 70° C. to 110° C. In the case that the reaction temperature exceeds 150° C., the activity of the catalyst might be lost. In the case that the reaction temperature is lower than 50° C., the reaction rate and productivity are low.

As the initiator in the present invention includes compounds represented by the formula (1) in which Z has a carbon number of 1 to 22 and the number x of hydroxyl group(s) is 1 to 6 and the compounds with methyloxirane added thereto. As the initiator, for example, butanol, butyl propylene glycol, polyoxypropylene glycol, polyoxypropylene glyceryl ether or the like. In the case that Z is $R^1OH$, as the initiator, it may be used a monovalent alcohol ($R^1OH$) having the hydrocarbon group having a carbon number of 1 to 22 represented by $R^1$, in the formula (5).

Although it is not particularly limited a small amount of water content contained in the initiator and methyl oxirane, the water contents contained in the initiator may preferably be 0.5 wt % or lower and contained in methyloxirane may preferably be 0.01 wt % or lower, respectively.

Although the used amount of the DMC catalyst is not particularly limited, it may preferably be 0.0001 to 0.1 wt % and more preferably be 0.001 to 0.05 wt % with respect to an amount of the generated alkyloxirane derivative. The DMC catalyst may be initially charged in batch or sequentially supplied in division into the reaction system. After the polymerization reaction, the composite metal complex catalyst is removed. The removal of the catalyst may be performed by known methods such as filtration, centrifugation or processing by means of a synthetic adsorption agent.

As the DMC catalyst used in the present invention, known catalysts may be used. For example, it may be represented by formula (6).

$$Ma[M'x(CN)y]b(H_2O)c(R)d \quad (6)$$

In the formula (6), M and M' represent metals, respectively, R represents an organic ligand, a, b, x and y are positive integers, respectively, which are changed depending on atomic values and ligand numbers of the metals, and c and d are positive integers, respectively, which are changed depending on the ligand numbers of the metals.

As the metal M, Zn (II), Fe(II), Fe (III), Co (II), Ni (II), Al (III), Sr (II), Mn (II), Cr (III), Cu (II), Sn (II), Pb (II), Mo (IV), Mo (VI), W (IV), W (VI) and the like are listed, and among them, Zn (II) is preferably used, As the metal M', Fe (II), Fe (II), C (II), Co (III), Cr (II), Cr (III), Mn (II), Mn (III), Ni (II), V (IV), V (V) and the like are listed, and among them, Fe (II), Fe (III), Co (II) and Co (III) are preferably used.

As the organic ligand R, an alcohol, ether, ketone, ester and the like are listed, and an alcohol is more preferred. Preferred organic ligands are of soluble in water, and specifically include t-butyl alcohol, n-butyl alcohol, iso-butyl alcohol, N,N-dimethyl acetoamide, ethylene glycol dimethyl ether (grime), diethylene glycol dimethyl ether (di-grime), and the like. $Zn_3[Co(CN)_6]_2$ having tert-butyl alcohol as the ligand is particularly preferred.

(Cosmetics)

The alkyloxirane derivative of the present invention may be blended into a cosmetic as a raw material for use in the cosmetic.

Particularly, in the case that the alkyloxirane derivative is blended in a hair cosmetic, particularly a treatment, the treatment is excellent in slippery feel during the washing of the treatment, slippery feel during the removal of water from hairs after the rinsing and smoothness of the hairs after the drying, and sticky feel is not left in the hairs. The derivative is thus useful.

The alkyloxirane derivative of the present invention is used in a cosmetic as an oily agent, and its concentration may preferably be 0.001 to 5 wt %. In the case that concentration of the alkyloxirane derivative is lower than 0.001 wt %, sufficiently high effects are not obtained. Further, in the case that the concentration exceeds 5 wt %, sticky feel is left during the drying, so that it is not preferable as a cosmetic.

Further, the cosmetic of the present invention may optionally contain liquid fate and oils, higher fatty acids, higher alcohols, silicones, esters, anionic surfactants, cationic surfactants, non-ionic surfactants, ampholytic surfactants, moisturizing agents, preservatives, pearl ingredients, pH conditioners, ultraviolet absorbing agents, hydrotropic agents, perfumes or the other kinds of ingredients.

(Hydraulic Oil Composition)

Then, the hydraulic oil composition of the present invention includes an ester compound (A) and the alkyloxirane derivative (B) described above, and 1.0 to 30.0 mass parts of the alkyloxirane derivative (B) is contained with respect to 100 mass parts of the ester compound (A).

(Eater Compound (A))

The ester compound (A) of the present invention is an ester compound of neopentyl polyol having a carbon number of 5 to 10 and an alcohol valence of 3 to 6 and of a fatty acid having a carbon number of 6 to 22.

As a raw material of the ester compound (A), it is used a neopentyl polyol having a carbon number of 5 to 10 and a alcohol valence of 3 to 6. The neopentyl polyol having a carbon number of 5 to 10 and a alcohol valence of 3 to 6 includes trimethylolpropane, pentaerythritol and dipentaerythritol, for example.

The neopentyl polyol as described above may preferably be trimethylolpropane or pentaerythritol, and more preferably be trimethylolpropane.

The fatty acid, having a carbon number of 6 to 22 as the raw material of the ester compound (A), may be a straight-chain and saturated fatty acid having a carbon number of 6 to 22, a branched-chain and saturated fatty acid having a carbon number of 6 to 22, or a straight-chain and unsaturated fatty acid having a carbon number of 6 to 22. In the case that the carbon number is less than 6, the lubricating property (wear resistance) may be deteriorated. The carbon number is thus made 6 or larger and more preferably 8 or larger. Further, in the case that the carbon number exceeds 22, the fuel consumption may be deteriorated by energy loss due to internal resistance of the lubricating oil itself provided by the high viscosity, and the thus generated ester may become a solid unusable as a lubricating oil. The carbon number is thus made 22 or less and more preferably 18 or less.

Specific examples of the straight-chain and saturated fatty acid include caproic acid, enanthic acid, caprylic acid, pelargonic acid, capric acid, lauric acid, myristic acid, palmitic acid, stearic acid, arachidic acid and behenic acid. Specific examples of the branched-chain and saturated fatty acids having a carbon number of 6 to 22 include 2-methyl pentanoic acid, 2-ethyl hexanoic acid, 3, 5, 5-trimethyl hexanoic acid and neodecanoic acid. Specific examples of the straight-chain and unsaturated fatty acid having a carbon number of 6 to 22 include palmitoleic acid, oleic acid, linoleic acid, linolenic acid and erucic acid.

The fatty acid described above may preferably be caproic acid, caprylic acid, capric acid, lauric acid, 2-ethyl hexanoic acid, 3, 5, 5-trimethyl hexanoic acid, oleic acid, linoleic acid or linolenic acid, and more preferably be caprylic acid, capric acid, 2-ethyl hexanoic acid, 3, 5, 5-trimethyl hexanoic acid or oleic acid.

(Alkyloxirane Derivative (B))

The alkyloxirane derivative (B) used in the present invention is the alkyloxirane derivative as described above.

Here, in the case that the average addition molar number n of the oxyalkylene group AO is less than 25, the viscosity becomes low and the lubricating property (wear resistance) may become insufficient. Thus, n is 25 or more and may preferably be 50 or more.

Further, as n is larger, the viscosity is increased. On the viewpoint of handling upon blending into the lubricating oil, n may preferably be 150 or less and more preferably be 120 or less.

Here, as $M_L/M_H$ of the alkyloxirane derivative is lower, the bias of the distribution of the molecular weight on the high molecular weight side is larger, so that an increase of the viscosity due to the bias is observed. In the case that $M_L/M_H$ is lower than 0.35, the viscosity becomes too high, so that it becomes difficult to blend it into the lubricating oil. On the viewpoint, $M_L/M_H$ is 0.35 or higher, and is preferably 0.36 or higher.

Further, As of the alkyloxirane derivative is made 0.70 or higher, the viscosity is increased, so that the lubricating property is improved in the case that the alkyloxirane derivative is blended into the lubricating oil. On the viewpoint, As is preferably made 0.65 or lower.

Further, as As is lower, the bias of the distribution of the molecular weight on the higher molecular weight side is larger, so that an increase of the viscosity due to the bias is observed. As is made 0.30 or higher, so that it is possible to suppress the increase of the viscosity and to blend the derivative into the lubricating oil easily. On the viewpoint, As may more preferably be 0.57 or higher.

(Composition of Hydraulic Oil Composition)

According to the present invention, 1.0 to 30.0 mass parts of the alkyloxirane derivative (B) is contained with respect to 100 mass parts of the ester compound (A). In the case that the content is lower than 1.0 mass part, the compatibility to a sealant may be insufficient. The content is thus made 1.0 mass part or higher, and may preferably be 5.0 mass part or higher. Further, in the case that the content of the alkyloxirane derivative (B) exceeds 30.0 mass parts, the viscosity of the whole of the hydraulic oil composition becomes high, so that the energy consumption may be deteriorated due to energy loss resulting from internal resistance in the lubricating oil itself. The content is thus made 30.0 mass parts or lower and is more preferably made 20.0 mass parts or lower.

(Active Energy Ray-Curable Resin Composition)

The active energy ray-curable resin composition of the present invention contains the following components (A) and (B), and a mass ratio ((A)/(B)) of a mass of the component (A) with respect to a mass of the component (B) is 1/99 to 30/70.

(Component (A): Urethane Compound)

The component (A) is an urethane compound of a reaction product of the alkyloxirane compound (a1) represented by the formula (1) and satisfying the relationship of formula (2) and of isocyanate (a2) having two or more isocyanate groups in the molecule.

As n of the alkyloxirane derivative is lower, the improvement of the workability is insufficient. n is thus made 25 or higher and more preferably 40 or higher. Further, as n is higher, the viscosity is increased so that its handling becomes difficult. n is thus preferably 150 or lower and more preferably 120 or lower.

The alkyloxirane derivative (a1) of the present invention satisfies $0.35 \le M_L/M_H \le 0.75$. In the case that $M_L/M_H$ exceeds 0.75, the distribution of molecular weight approaches symmetrical pattern in the right and left sides, so that the effect of resistance against impact is deteriorated. $M_L/M_H$ is thus made 0.75 or lower and preferably 0.62 or lower.

Further, in the case that $M_L/M_H$ is lower than 0.35, the bias of the distribution of molecular weight is larger on the side of higher molecular weight, so that the viscosity becomes too high and its handling is difficult. $M_L/M_H$ is thus made 0.35 or higher and preferably 0.36 or higher.

The isocyanate (a2) of the present invention is an isocyanate having two or more isocyanate groups in the molecule. Specific examples of the difunctional isocyanate include aliphatic and alicyclic diisocyanates such as trimethylene diisocyanate, hexamethylene diisocyanate, 1,4-cyclohexane diisocyanate, dicyclohexyl methane diisocyanate, isophorone diisocyanate, norbornane diisocyanate; and aromatic isocyanates such as 1, 4-tolylene diisocyanate, 2,4-tolylene diisocyanate, 2,6-tolylene diisocyanate, 1,3-xylilene diisocyanate, 1,5-naphthalene diisocyanate, 4,4'-diphenylmethane diisocyanate or the like.

Specific examples of trifunctional isocyanates include isocyanurate products obtained by polycondensation reaction and the resulting isocyanurate modification of a diisocyanate such as 1,4-tolylene diisocyanate, 2,4-tolylene diisocyanate, 2,6-tolylene diisocyanate, 1,3-xylylene diisocyanurate, hexamethylene diisocyanate, dicyclohexyl methane diisocyanate, isophorone diisocyanate, norbornane diisocyanate or the like; an adduct obtained by subjecting the diisocyanate described above to adduct modification; and a biuret product obtained by subjecting the diisocyanate described above and a trivalent alcohol such as glycerin or trimethylolpropane to biuret modification.

Specific examples of multi-functional isocyanate containing four or more isocyanate groups include an isocyanate compound obtained by reacting the diisocyanate described above and a polyol or a polyamine.

The component (A) of the present invention is an urethane compound obtained by the urethane reaction of the alkyloxirane derivative (a1) and of the aliphatic, alicyclic or aromatic isocyanate (a2) having two or more isocyanate groups in a molecule.

In the urethane reaction, as to the ratio of the components (a1) and (a2), normally 0.1 to 10 equivalents of, preferably 0.1 to 5 equivalent of and more preferably 0.3 to 1.0 equivalents of isocyanate group of the polyisocyanate (a2) is contained with respect to 1 equivalent of hydroxyl group in the component (a1). The reaction temperature is normally 20 to 150° C., preferably 30 to 100° C. and more preferably 40 to 80° C. Further, the end point of the reaction can be confirmed by disappearance of infrared absorption spectrum at 2270 $cm^{-1}$ corresponding to the isocyanate group or by measuring the content of the isocyanate group according to the method described in JIS K 7301.

Further, a catalyst may be used for improving the reaction rate in the urethane reaction. Specific examples of the urethane catalysts include tin compounds such as dibutyl tin dilaurate, dioctyl tin dilaurate or the like, and zirconium compounds such as zirconium acetylacetonate, zirconium dibutoxy bis(ethyl acetoacetate) or the like. These catalysts can be also used in the urethane reaction in the present invention.

(Component (B))

The active energy ray-curable composition of the present invention contains the component (B) as an effective component. The component (B) used in the present invention is an urethane (meth)acrylate having two or more ethylenically unsaturated groups.

The urethane (meth)acrylate having two or more ethylenically unsaturated groups is normally obtained by reacting a polyisocyanate and a (meth)acrylate having a hydroxyl group so as to generate two or more ethylenically unsaturated groups, and a polyol compound may optically be reacted.

The polyisocyanate includes: an aromatic polyisocyanate such as tolylene diisocyanate, diphenylmethane diisocyanate, polyphenyl methane diisocyanate, modified diphenylmethane diisocyanate, xylylene diisocyanate, tetramethyl xylylene diisocyanate, phenylene diisocyanate, naphthalene diisocyanate or the like; an aliphatic polyisocyanate such as pentamethylene diisocyanate, hexamethylene diisocyanate, trimethyl hexamethylene diisocyanate, lysine diisocyanate, lysine triisocyanate or the like; an alicyclic polyisocyanate such as hydrogenated diphenylmethane diisocyanate, hydrogenated xylylene diisocyanate, isophorone diisocyanate, norbornene diisocyanate, 1,3-bis(isocyanate methyl) cyclohexane or the like; and a trimer compound, multimer compound, allophanate type polyisocyanate, burette type polyisocyanate, water-dispersible type polyisocyanate or the like of each of the above polyisocyanates.

As the meth(acrylate) having the hydroxyl group described above, it is used a (meth)acrylate having one hydroxyl group and at least one (meth)acryloyl group in the molecule. For example, it includes: a hydroxyalkyl (meth) acrylate such as 2-hydroxyethyl (meth)acrylate, 2-hydroxypropyl (meth) acrylate, 2-hydroxybutyl (meth)acrylate, 4-hydroxybutyl (meth) acrylate, 6-hydroxyhexyl (meth) acrylate) or the like; hydroxyl group-containing (meth) acrylate compounds having one ethylenically unsaturated group such as 2-hydroxyethyl acryloyl phosphate, 2-(meth) acryloloxy-ethyl-2-hydroxypropyl phthalate, caprolactone-modified 2-hydoxyethyl (meth) acrylate, dipropylene glycol (meth) acrylate, fatty acid-modified glycidyl (meth) acrylate, polyethylene glycol mono(meth) acrylate, polypropylene glycol mono(meth)acrylate, 2-hydroxy-3-(meth) acryloloxypropyl (meth)acrylate or the like; hydroxyl group-containing (meth)acrylate compound having two ethylenically unsaturated groups such as glycerin di(meth) acrylate, 2-hydroxy-3-acryloil-oxypropyl methacrylate or the like; and hydroxyl group-containing (meth)acrylate compound having three or more ethylenically unsaturated groups such as pentaerythritol tri(meth)acrylate, caprolactone-modified pentaerythritol tri(meth)acrylate, ethylene oxide-modified pentaerythritol tri(meth)acrylate, dipentaerythritol penta(meth)acrylate, caprolactone-modified dipentaerythritol penta(meth)acrylate, ethylene oxide-modified dipentaerythritol penta(meth)acrylate or the like.

The polyol compound includes, for example, an aliphatic polyol, alicyclic polyol, polyether-series polyol, polyester-series polyol, polycarbonate-series polyol, polyolefin-series polyol, polybutadiene-series polyol, (meth)acrylate-series polyol, polysiloxane-series polyol, or the like.

The urethane (meth)acrylate having two or more ethylenically unsaturated groups of the above component (B) can be produced by reacting the respective components by known reaction methods.

It can conventionally be produced by charging the above polyisocyanate, hydroxyl group-containing (meth)acrylate, and optionally polyol compound in a batch or separately in a reactor, and by performing urethane reaction by a known method. In the case that the polyol compound is used, it is useful the method of producing it by reacting the polyol compound and polyisocyanate compound with each other in advance to obtain reaction product, which is then reacted with the hydroxyl group-containing (meth)acrylate, on the viewpoint of stability of the urethane reaction and reduction of by-products.

In the urethane reaction, the reaction may be terminated at the time point that a content of the residual isocyanate group is 0.5 mass percent or lower, so that it is obtained the urethane (meth)acrylate having two or more ethylenically unsaturated groups.

Further, in the urethane reaction, it is preferred to use a catalyst for promoting the reaction. Such catalyst includes: for example, organic metal compounds such as dibutyl tin dilaurate, dibutyl tin diacetate, trimethyl tin hydroxide, tetra-n-butyl tin, zinc bisacetyl acetonate, zirconium tris (acetoacetonate)ethyl acetoacetate, zirconium tetraacetyl acetonate or the like; metal salts such as tin octanoate, zinc hexanoate, zinc octenoate, zinc stearate, zirconium 2-ethyl hexanoate, cobalt naphthenate, stannous chloride, stannic chloride, potassium acetate or the like; amine based catalysts such as triethylamine, triethylenediamine, benzyl diethyl amine, 1, 4-diazabicyclo [2,2,2] octane, 1,8-diazabicycle [5,4,0] undecene, N,N,N',N'-tetramethyl-1,3-butane diamine, N-methyl morpholine, N-ethyl morpholine or the like; and bismuth-based catalysts such as bismuth nitrate, bismuth bromide, bismuth iodide, bismuth sulfide, organic bismuth compounds such as dibutyl bismuth dilaurate, dioctyl bismuth dilaurate, and organic bismuth salts such as bismuth salt of 2-ethyl hexanoic acid, bismuth salt of naphtenic acid, bismuth salt of isodecanoic acid, bismuth salt of neodecanoic acid, bismuth salt of lauric acid, bismuth salt of maleic acid, bismuth salt of stearic acid, bismuth salt of oleic acid, bismuth salt of linoleic acid, bismuth salt of acetic acid, bismuth libis neodecanoate, bismuth disalycilate, bismuth subgallate or the like. Among them, dibutyl tin dilaurate and 1,8-diazabicyclo[5, 4, 0]undecene are preferred. These may be used alone or two kinds of them may be used in combination.

In the urethane reaction, it may be used an organic solvent free from a functional group capable of reacting with isocyanate group, including: esters such as ethyl acetate, butyl acetate or the like; ketones such as methyl ethyl ketone, methyl isobutyl ketone or the like; or aromatics such as toluene, xylene or the like.

Further, the reaction temperature is normally 30 to 90° C. and preferably 40 to 80° C. The reaction time is normally 2 to 10 hours and preferably 3 to 8 hours. Two or more kinds of the urethane (meth)acrylate having two or more ethylenically unsaturated groups of the above component (B) may be mixed and used.

(Compositional ratios of active energy ray-curable resin composition) In the resin composition of the present invention, a mass ratio of the mass of the component (A) with respect to a mass of the component (B) ((A)/(B)) is 1/99 to 30/70, preferably 2/98 to 20/80, and more preferably 5/95 to 12/88. In the case that the ratio ((A)/(B)) of the mass of the component (A) with respect to that of the component (B) is less than 1/99, the resistance against impact is deteriorated. On the other hand, the mass ratio ((A)/(B)) exceeds 30/70, there is no such additional effect on the resistance against impact.

(Photo Initiator)

A photo initiator may be blended into the curable resin composition of the present invention. As the photo initiator, for example, benzoin or benzoin alkyl ether such as benzoin, benzoin methyl ether or the like; aromatic ketones such as benzophenone, benzoyl benzoic acid or the like; benzyl ketals such as benzyl dimethyl ketal, benzyl diethyl ketal or the like; acetophenones such as 1-hydroxy cyclohexyl phenyl ketone, 2-hydroxy-2-methyl-1-phenyl-1-propane-1-one or the like; and acyl phosphine oxides such as 2,4,6-trimethyl benzoyl diphenyl phosphine oxide, bis(2,4,6-trimethyl benzoyl) phenyl phosphine oxide or the like.

(The Other Components)

Further, the curable resin composition of the present invention may optionally contain (meth)acrylic polymer, surface adjusting agent, levelling agent, filler, pigment, silane coupling agent, antistatic agent, anti-foamer, antifouling agent, anti-oxidants, ultrasonic ray absorber, photo stabilizer, photo initiator, organic solvent or the like.

As methods of curing the inventive curable resin composition, it may be selected an active ray from the group consisting of infrared ray, visible ray, ultraviolet ray, X-ray, γ-ray and electron ray. As methods of irradiating the active energy ray, it may be used a conventional method of curing a curable resin composition. In the case that ultraviolet ray is used as a system for irradiating active energy ray, it may be used a non-electrode lamp, low pressure mercury lamp, high pressure mercury lamp, ultrahigh pressure mercury lamp, xenon lamp, gallium lamp, metal halide lamp or the like having spectrum in a wavelength range of 200 to 450 nm such as H valve supplied by Fusion UV Systems co. Ltd. The amount of irradiation of the active energy ray is normally 10 to 3000 mJ/cm$^2$, preferably 50 to 2000 mJ/cm$^2$, and more preferably 100 to 1000 mJ/cm$^2$, as integrated light amount. An atmosphere during the irradiation may be air, or the curing may be performed in an inert gas atmosphere such as nitrogen or argon.

(Oil Cleansing Agent)

The oil cleansing agent of the present invention contains the following components (a), (b) and (c).

(Component (a))

The alkyloxirane derivative of the component (a) is the alkyloxirane derivative described above represented by the formula (1) and satisfying the formulas (2) to (4).

Here, in the case that n is less than 25, the slippery feel in the application and moisture feel of the skin after the washing may possibly be insufficient. On the viewpoint, n is 25 or higher and more preferably 50 or higher.

Further, as n is higher, the viscosity of the composition is increased and the handling performance is deteriorated. On the viewpoint of handling performance, n may preferably be 150 or lower and more preferably be 120 or lower.

The alkyloxirane derivative of the present invention satisfies the formula of $0.35 \leq M_L/M_H \leq 0.75$. In the case that $M_L/M_H$ exceeds 0.75, the viscosity of the alkylozirane derivative is lowered, and in the case that it is blended into an oil cleansing agent, sufficiently high rinsing property is not realized. On the viewpoint, $M_L/M_H$ is 0.75 or lower and more preferably 0.62 or lower.

Further, as $M_L/M_H$ is lower, the bias of the distribution of the molecular weight on the higher molecular weight side is enlarged, so that it is observed an increase of the viscosity due to this. In the case that $M_L/M_H$ is lower than 0.35, the viscosity is too high and the handling performance is deteriorated. On the viewpoint, $M_L/M_H$ is 0.35 or higher, and preferably 0.36 or higher.

Further, As of the alkyloxirane derivative is made 0.70 or lower, the viscosity is improved and the moisture feel can be advantageously provided on the skin after washing. On the viewpoint, As may more preferably be 0.65 or lower.

Further, as As is lower, the bias of the distribution of the molecular weight on the side of the higher molecular weight becomes large, resulting in an increase of the viscosity due to this. Thus, As is made 0.30 or higher on the viewpoint of handling performance, As is more preferably 0.57 or higher.

According to the present invention, the content of the component (a) is made 1 to 20 mass percent, provided that 100 mass percent is assigned to a total content of the components (a), (b) and (c). In the case that the content of the component (a) is less than 1 mass percent, elongation at the initiation of application, slippery feel in use and moisture feel of skin after washing are insufficient, and is thus made 1 mass percent or higher. Further, in the case that the content of the component (a) exceeds 20 mass percent, the elongation at the initiation of application and slippery feel in use are deteriorated. It is thus made 20 mass percent or lower and preferably 10 mass percent or lower.

(Component (b): Liquid Oily Component)

The component (b) is a liquid oily component. The liquid oily component means an oily component being liquid at 25° C. It includes, for example, ester oils such as diethyl sebacate, cetyl 2-ethylhexanoate, isopropyl palmitate, 2-ethylhexayl palmitate, octyl dodecyl myristate, isopropyl myristate, isodecyl isononanoate, ethyl oleate, jojoba oil or the like; plant oils such as olive oil, macadamia nut oil, sun seed oil or the like; hydrocarbon oils such as liquid paraffin, liquid isoparaffin, squalene or the like; and silicone oils such as dimethyl polysiloxane, polymethyl cyclosiloxane, polyether-modified methyl polysiloxane or amino-modified dimethylpolysiloxane. A single kind or two or more kinds of them may be selected and used.

As the component (b), it is preferred to use the ester oil or plant oil, and more preferred to use both of the plant oil and ester oil, and in this case, it is preferred that the ratio of the mass of the plant oil and mass of the ester oil satisfies the following formula (7). In this case, it is most preferred that 2-ethylhexyl palmitate is used as the ester oil and olive oil is used as the plant oil, for sufficiently obtaining the effects of the present invention.

$$1.5 \leq \text{mass of plant oil/mass of ester oil} \leq 2.0 \quad (7)$$

According to the present invention, the content of the component (b) is made 45 to 90 mass percent, provided that 100 mass percent is assigned to a total content of the components (a), (b) and (c). In the case that the content of the component (b) is less than 45 mass percent, the elongation at the initiation of the application and cleansing performance are insufficient. It is thus made 45 mass percent or higher, and more preferably 55 mass percent or higher. Further, in the case that the content of the component (b) exceeds 90 mass percent, although the elongation at the initiation of the application and cleansing performance are better, the rinsing performance is deteriorated. It is thus made 90 mass percent or lower, and more preferably 70 mass percent or lower.

(Component (c): Surfactant of Ester of Polyvalent Alcohol and Fatty Acid)

The component (c) is a surfactant of an eater of a polyvalent alcohol and fatty acid. The surfactant is composed of an ester of the polyvalent alcohol and fatty acid.

Here, the number of the hydroxyl value of the polyvalent alcohol constituting the component (c) is preferably 3 or more. Although the upper limit of the hydroxyl number of the polyvalent alcohol constituting the component (c) is not particularly defined, it may preferably be 12 or lower and more preferably be 6 or lower. The fatty acid for forming the component (c) may preferably have a carbon number of 8 to 18.

As the component (c), for example, it may be listed sorbitan monolaurate, sorbitan monopalmitate, sorbitan monostearate, sorbitan monooleate, sorbitan sesquioleate, sorbitan trioleate, glycerin monostearate, glycerin monooleate, polyglyceryl monolaurate, polyoxyethylene glyceryl (caprylic acid/capric acid), polyoxyethylene glyceryl coconut oil fatty acid, polyoxyethylene glyceryl isostearate, polyoxyethylene glyceryl triisostearate, polyoxyethylene sorbit tetraoleate, polyoxyethylene sorbit tetraisostearate, polyethylene sorbit isostearate, polyoxyethylene sorbit pentaoleate or the like. A single kind or two or more kinds of non-ionic surfactants of the esters of the polyvalent alcohols and fatty acid may be selected and used.

More preferably, it is possible to improve the cleansing performance, by combining the component (c) having a low HLB and the component (c) having a high HLB. Specifically, it is preferred that the component (c) having a low HLB has an HLB range of 4 or higher and below 10, that the component (c) having a high HLB has an HLB range of 10 or higher and below 15, and that the component (c) having the low HLB and the component (c) having the high HLB are used in combination.

The content of the component (c) is made 5 to 50 mass percent, provided that 100 mass percent is assigned to a total content of the components (a), (b) and (c). In the case that the content of the component (c) is below 6 mass percent, the slippery feel in use and rinsing performance are insufficient. It is thus made 5 mass percent or higher, and more preferably 20 mass percent or higher. Further, in the case that the content of the component (c) exceeds 50 mass percent, the moisture feel of the skin after washing is deteriorated. It is thus made 50 mass percent or lower and more preferably be 35 mass percent or lower.

On the viewpoint of improving elongation at the initiation of application, slippery feel in use and moisture feel of the skin after washing, the mass ratio (a/c) of the component (a) with respect to the component (c) may preferably be 1 or lower and more preferably 0.05 to 0.45.

Further, it is possible to blend water or an additive conventionally used in cosmetics to the oil cleansing agent of the present invention, as long as the effects of the present invention are not lost. For example, the additives includes oily bases such as ceramide, cholesterol, protein derivative, lanoline, lanoline derivative, lecithin or the like; waxes such as beeswax, carnauba wax or the like; anionic surfactants such as soap, acyl methyl taurine salt, amide ether sulfate ester or the like; ampholytic surfactants such as amide amino salt, amide propyl dimethyl amino acetic acid betaine or the like; semi-polar surfactants such as alkyl chloride; water soluble macromolecules such as alginic acid, carboxyvinyl polymer, carboxy methyl cellulose, hydroxy propyl methyl cellulose, hydroxy ethyl cellulose, xanthan gum or the like; organic and inorganic salts such as pyrrolidone carboxylic acid salts, citrates, malates, table salt or the like; acids and alkalis as pH adjusting agents; fungicides; chelating agents; anti-oxidants; ultraviolet ray absorbers; vitamins; natural essences derived from animals and plants; colorants; pigments or the like.

EXAMPLES

Experiment A: Hair Cosmetics

The present invention will be described further in detail below.

Reference Synthetic Example: Synthesis of a Catalyst of a Complex of a Composite Metal Cyanide Into 2.0 ml of aqueous solution containing 2.1 g of zinc chloride, 15 ml of aqueous solution containing 0.84 g of potassium hexacyano cobaltate $K_3 Co(CN)_6$ was added dropwise at 400 for 15 minutes while stirring. After the addition in dropwise, 16 ml of water and 16 g of tert-butyl alcohol were added and the temperature was elevated to 70° C., followed by stirring for 1 hour. After the cooling to room temperature, filtration (first-time filtration) was performed to obtain solid. 14 ml of water and 8.0 g of tert-butyl alcohol were added to the solid, followed by agitation for 30 minutes and filtration (second-time filtration) to obtain solid.

Further, 18.6 g of tert-butyl alcohol and 1.2 g of methanol were added to the solid again, followed by agitation for 30 minutes and filtration (third-time filtration) to obtain solid. The thus obtained solid was dried at 40° C. under reduced pressure for 3 hours to obtain 0.7 g of catalyst of a complex of composite metal cyanide.

Synthetic Example 1

Into a 5-liter (inner volume of 4890 ml) of a stainless pressure-proof bath equipped with a thermometer, pressure gauge, security valve, tube for blowing nitrogen gas, agitator, vacuum discharge tube, cooling coil and vacuum jacket, 200 g of n-butanol and 0.2 g of the complex catalyst of the composite metal cyanide of the reference example were charged. After replacement with nitrogen, the temperature was elevated to 110° C. 243 g of methyloxirane (supplied by Sumitomo Chemical Co. Ltd.; LOT. 151211D) was charged under condition of 0.3 MPa or lower through the tube for blowing nitrogen gas over 16 hours. At the time, it was measured the change of pressure and temperature in the reaction bath over time.

After 16 hours, the pressure in the reaction bath was rapidly lowered. Thereafter, the temperature in the reaction bath was maintained at 110° C., and methyloxirane was gradually charged through the tube for blowing nitrogen gas under condition of 0.6 MPa or lower. A total amount of 3,270 g of methyloxirane was continuously added under pressure and agitation. At this time, the time for supplying 987 g of methyloxirane was 60 minutes, time for supplying 2,470 g of methyloxirane was 180 minutes and time for supplying 3,270 g was 270 minutes.

After the termination of the addition, the reaction was performed at 110° C. for 1 hour. 2220 g of product was drawn from the reaction bath and the temperature of the remaining product in the reaction bath was elevated to 110° C. 1,110 g of methyloxirane was then added under condition of 0.6 MPa or lower through the tube for blowing nitrogen gas for 2 hours. After the termination of the addition, the reaction was performed at 110° C. for 1 hour. 1,044 g of product was drawn from the reaction bath again, and the temperature of the product remaining in the reaction bath was elevated to 110° C. 312 g of methyloxirane was added for 40 minutes under condition of 0.6 MPa or lower through the tube for blowing nitrogen gas. After the termination of the addition, the reaction was performed at 110° C. for 1 hour, followed by the treatment under reducing pressure at 75 to 85° C. and 50 to 100 Torr for 1 hour while nitrogen gas was blown and by subsequent filtration. The thus obtained reaction product (synthetic example 1) was subjected to gel permeation chromatography.

Figure 3:
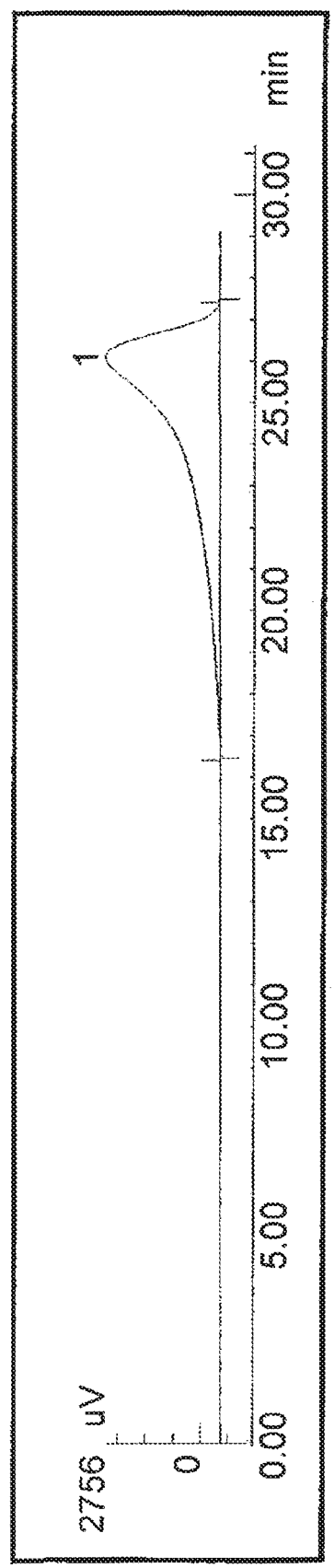
FIG. 3 is a chromatogram obtained in synthetic example 1.

As to the gel permeation chromatography, as the system, "S HODEX GPC101GPC" dedicated system, "SHODEX RI-71s" as the differential refractometer, and "SHODEX KF-GS" was used as a guard column. Three columns of "HODEX KF804L" were continuously equipped as the columns, the temperature of the columns was made 40° C., tetrahydrofuran was flown at a flowing rate of 1 ml/minute as a developing solvent, 0.1 ml of tetrahydrofuran solution of the thus obtained reaction product of a content of 0.1 mass percent was injected and "BORWIN GPC calculation program" was used to obtain the chromatogram represented by the intensity of the refractive index and elution time. FIG. 3 is the thus obtained chromatogram. $M_L/M_H$ and As were calculated from the chromatogram and proved to be 0.52 and 0.58, respectively.

Synthetic Examples 2 to 6

Into a 5-liter (inner volume of 4890 ml) of a stainless pressure-proof reaction bath equipped with a thermometer, pressure gauge, security valve, tube for blowing nitrogen gas, agitator, vacuum discharge tube, cooling coil and vacuum jacket, 200 g of butyl propylene glycol and 0.2 g of the complex catalyst of the composite metal cyanide of the reference example were charged. After replacement with nitrogen, the temperature was elevated to 110° C. 210 g of methyloxirane was charged under condition of 0.3 MPa or lower through the tube for blowing nitrogen gas over 4 hours. At this time, it was measured the change of pressure and temperature in the reaction bath over time.

After 4 hours, the pressure in the reaction bath was rapidly lowered. Thereafter, the temperature in the reaction bath was maintained at 110° C., and methyloxirane was gradually charged through the tube for blowing nitrogen gas under condition of 0.6 MPa or lower. A total amount of 3,287 g of methyloxirane was continuously added under pressure and agitation. At the time, the time for supplying 840 g of methyloxirane was 60 minutes, time for supplying 2,100 g of methyloxirane was 108 minutes and time for supplying 3,287 g was 132 minutes.

After the termination of the addition, the reaction was performed at 110° C. for 1 hour. 1,680 g of product was drawn from the reaction bath. The temperature of the remaining product in the reaction bath was elevated to 110° C. 696 g of methyloxirane was then added under condition of 0.6 MPa or lower through the tube for blowing nitrogen gas for 77 minutes. After the termination of the addition, the reaction was performed at 110° C. for 1 hour. 1,188 g of the product was drawn from the reaction bath again, followed by the treatment under reducing pressure at 75 to 85° C. and 50 to 100 Torr for 1 hour while nitrogen gas was blown and by subsequent filtration.

The thus obtained reaction product (synthetic example 2) was subjected to gel permeation chromatography. As a result, $M_L/M_H$ and As were proved to be 0.62 and 0.65, respectively.

Further, the temperature of the remaining product in the reaction bath was elevated to 110° C. 291 g of methyloxirane was then added under condition of 0.6 MPa or lower through the tube for blowing nitrogen gas for 35 minutes, while the temperature in the reaction bath was maintained at 110° C. After the termination of the addition, the reaction was performed at 110° C. for 1 hour. 752 g of product was drawn from the reaction bath again. The treatment under reducing pressure was performed at 75 to 85° C. and 50 to 100 Torr for 1 hour while nitrogen gas was blown, followed by filtration. The thus obtained reaction product (synthetic example 3) was subjected to gel permeation chromatography. As a result, $M_L/M_H$ and As were proved to be 0.58 and 0.63, respectively.

Further, the temperature of the remaining product in the reaction bath was elevated to 110° C. 174 g of methyloxirane was then added under condition of 0.6 MPa or lower through the tube for blowing nitrogen gas for 20 minutes, while the temperature in the reaction bath was maintained at 110° C. After the termination of the addition, the reaction was performed at 110° C. for 1 hour. 619 g of product was drawn from the reaction bath again. The treatment under reducing pressure was performed at 75 to 85° C. and 50 to 100 Torr for 1 hour while nitrogen gas was blown, followed by filtration. The thus obtained reaction product (synthetic example 4) was subjected to gel permeation chromatography. As a result, $M_L/M_H$ and As were proved to be 0.52 and 0.61, respectively.

Further, the temperature of the remaining product in the reaction bath was elevated to 110° C. 121 g of methyloxirane was then added under condition of 0.6 MPa or lower through the tube for blowing nitrogen gas for 30 minutes, while the temperature in the reaction bath was maintained at 110° C. After the termination of the addition, the reaction was performed at 110° C. for 1 hour. 370 g of product was drawn from the reaction bath again. The treatment under reducing pressure was performed at 75 to 85° C. and 50 to 100 Torr for 1 hour while nitrogen gas was blown, followed by filtration. The thus obtained reaction product (synthetic example 5) was subjected to gel permeation chromatography. As a result, $M_L/M_H$ and As were proved to be 0.42 and 0.59, respectively.

Further, the temperature of the remaining product in the reaction bath was elevated to 110° C. 122 g of methyloxirane was then added under condition of 0.6 MPa or lower through the tube for blowing nitrogen gas for 30 minutes, while the temperature in the reaction bath was maintained at 110° C. After the reaction was performed at 110° C. for 1 hour, the treatment under reducing pressure was performed at 75 to 85° C. and 50 to 100 Torr for 1 hour while nitrogen gas was blown, followed by filtration. The thus obtained reaction product (synthetic example 6) was subjected to gel permeation chromatography. As a result, $M_L/M$ and As were proved to be 0.36 and 0.57, respectively.

Synthetic Examples 7 and 8

Into a 5-liter (inner volume of 4890 ml) of a stainless pressure-proof reaction bath equipped with a thermometer, pressure gauge, security valve, tube for blowing nitrogen gas, agitator, vacuum discharge tube, cooling coil and vacuum jacket, 200 g of polyoxypropylene glycol having a molecular weight of 700 and obtained by reacting propylene glycol and methyloxirane and 0.1 g of the complex catalyst of the composite metal cyanide of the reference example were charged. After replacement with nitrogen, the temperature was elevated to 110° C. 145 g of methyloxirane was charged under condition of 0.3 MPa or lower through the tube for blowing nitrogen gas over 3 hours. At the time, it was measured the change of pressure and temperature in the reaction bath over time.

After 3 hours, the pressure in the reaction bath was rapidly lowered. Thereafter, the temperature in the reaction bath was maintained at 110° C., and methyloxirane was gradually charged through the tube for blowing nitrogen gas under condition of 0.6 MPa or lower. A total amount of 1,230 g of methyloxirane was continuously added under pressure and agitation. At this time, the time for supplying 130 g of methyloxirane was 10 minutes, time for supplying 540 g of methyloxirane was 55 minutes and time for supplying 1,230 g was 60 minutes.

After the termination of the addition, the reaction was performed at 110° C. for 1 hour. 550 g of product was drawn from the reaction bath. The treatment under reducing pressure was performed at 75 to 85° C. and 50 to 100 Torr for 1 hour while nitrogen gas is blown, followed by filtration. The thus obtained reaction product (synthetic example 7) was subjected to gel permeation chromatography. As a result, $M_L/M_H$ and As were proved to be 0.65 and 0.65, respectively.

Further, the temperature of the remaining product in the reaction bath was elevated to 110° C. 870 g of methyloxirane was then added under condition of 0.6 MPa or lower through the tube for blowing nitrogen gas for 80 minutes, while the temperature in the reaction bath was maintained at 110° C. After the reaction was performed at 110° C. for 1 hour, the treatment under reducing pressure was performed at 75 to 85° C. and 50 to 100 Torr for 1 hour while nitrogen gas was blown, followed by filtration. The thus obtained reaction product (synthetic example 8) was subjected to gel permeation chromatography. As a result, $M_L/M_H$ and As were proved to be 0.6 and 0.6, respectively.

Synthetic Examples 9 to 11

Into a 5-liter (inner volume of 4890 ml) of a stainless pressure-proof reaction bath equipped with a thermometer, pressure gauge, security valve, tube for blowing nitrogen gas, agitator, vacuum discharge tube, cooling coil and vacuum jacket, 100 g of polyoxypropylene glycol glyceryl ether having a molecular weight of 510 and obtained by reacting glycerin and methyloxirane and 0.05 g of the complex catalyst of the composite metal cyanide of the reference example were charged. After replacement with nitrogen, the temperature was elevated to 110° C. 50 g of methyloxirane was charged under condition of 0.3 MPa or lower through the tube for blowing nitrogen gas over 6 hours. At this time, it was measured the change of pressure and temperature in the reaction bath over time.

After 5 hours, the pressure in the reaction bath was rapidly lowered. Thereafter, the temperature in the reaction bath was maintained at 110° C., and methyloxirane was gradually charged through the tube for blowing nitrogen gas under condition of 0.6 MPa or lower. A total amount of 690 g of methyloxirane was continuously added under pressure and agitation. At the time, the time for supplying 150 g of methyloxirane was 20 minutes, time for supplying 370 g of methyloxirane was 15 minutes and time for supplying 690 g was 30 minutes.

After the termination of the addition, the reaction was performed at 110° C. for 1 hour. 480 g of product was drawn from the reaction bath. The treatment under reducing pressure was performed at 75 to 85° C. and 50 to 100 Torr for 1 hour while nitrogen gas is blown, followed by filtration. The thus obtained reaction product (synthetic example 9) was subjected to gel permeation chromatography. As a result, $M_L/M_H$ and As were proved to be 0.65 and 0.66, respectively.

Further, the temperature of the remaining product in the reaction bath was elevated to 110° C. 180 g of methyloxirane was then added under condition of 0.6 MPa or lower through the tube for blowing nitrogen gas for 20 minutes, while the temperature in the reaction bath was maintained at 110° C. After the reaction was performed at 110 t for 1 hour, the treatment under reducing pressure was performed at 75 to 85° C. and 50 to 100 Torr for 1 hour while nitrogen gas was blown, 200 g of the product was then drawn from the reaction bath again, and the treatment under reducing pressure was performed at 75 to 85° C. and 60 to 100 Torr for 1 hour while nitrogen gas was blown, followed by filtration. The thus obtained reaction product (synthetic example 10) was subjected to gel permeation chromatography. As a result, $M_L/M_H$ and As were proved to be 0.64 and 0.64, respectively.

Further, the temperature of the remaining product in the reaction bath was elevated to 110° C. 140 g of methyloxirane was then added under condition of 0.6 MPa or lower through the tube for blowing nitrogen gas for 20 minutes, while the temperature inside of the reaction bath was maintained at 110° C. After the reaction was performed at 110° C. for 1 hour, the treatment under reducing pressure was performed at 75 to 85° C. and 50 to 100 Torr for 1 hour while nitrogen gas was blown, followed by filtration. The thus obtained reaction product (synthetic example 11) was subjected to gel permeation chromatography. As a result, $M_L/M_H$ and As were proved to be 0.62 and 0.61, respectively.

Comparative Synthetic Example 1

Into a 5-liter (inner volume of 4890 ml) of a stainless pressure-proof reaction bath equipped with a thermometer, pressure gauge, security valve, tube for blowing nitrogen gas, agitator, vacuum discharge tube, cooling coil and vacuum jacket, 5.4 g of potassium hydroxide and 250 g of polyoxypropylene butyl ether with a molecular weight of 1,290 and obtained by reacting with methyloxirane. 2,322 g of methyloxirane was reacted at 100° C. and the remaining methyloxirane was removed under reduced pressure at 0° C. for 30 minutes. The reaction product was moved into a 5-liter eggplant flask and promptly neutralized by 1N hydrochloric acid, followed by dehydration under nitrogen atmosphere and filtration.

Figure 4:
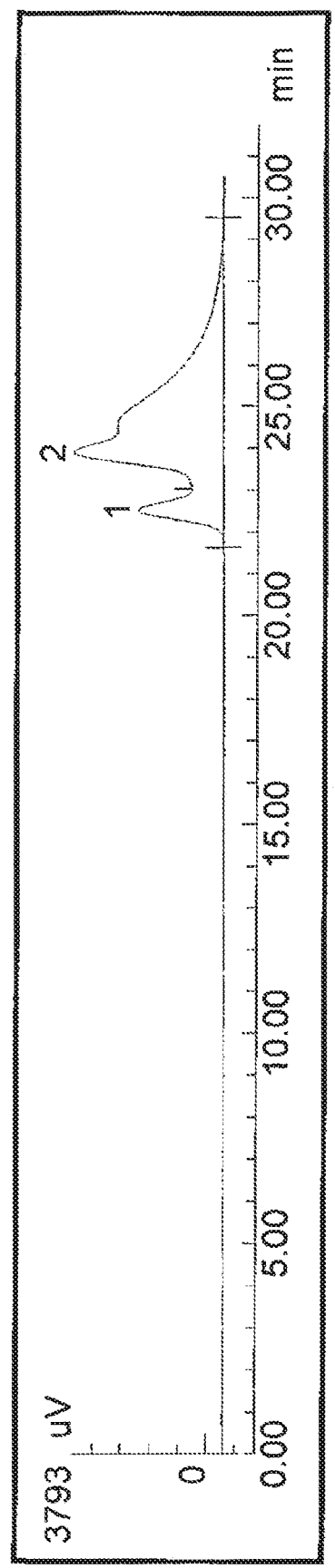
FIG. 4 is a chromatogram obtained in comparative synthetic example 1.

The thus obtained reaction product (comparative synthetic example 1) was subjected to measurement by gel permeation chromatography. FIG. 4 shows the thus obtained chromatogram.

Tables 1 and 2 indicate values of $M_L/M_H$ and As calculated from chromatograms, together with the properties of compounds of the synthetic examples 1 to 11, comparative synthetic example 1, and "PREMINOL S1004F" (supplied by AGC Inc., high molecular weight·low by-product polyether polyol, number of functional groups is 1) and "PREMINOL S4013F" (supplied by AGC Inc., high molecular weight·low by-product polyether polyol, number of functional groups is 2) in table 2.

Further, in the case of the comparative synthetic example 1, "PREMINOL S1004F" and "PREMINOL S4013F", the number of the maximum points of the refractive index in the chromatogram is not one and unimodal peak is not provided. It is thus shown values of $M_L/M_H$ and As in the peak of the maximum point having the maximum intensity of the refractive index.

In tables 1 and 2, hydroxyl values, kinematic viscosities and unsaturation degrees were measured according to JIS K-1557-1, JIS K-2283 and JIS K-1557, respectively. Molecular weights were calculated based on the hydroxyl values.

TABLE 1

|  | Synthetic Example 1 | Synthetic Example 2 | Synthetic Example 3 | Synthetic Example 4 | Synthetic Example 5 | Synthetic Example 6 |
|---|---|---|---|---|---|---|
| $M_L/M_H$ | 0.52 | 0.62 | 0.58 | 0.52 | 0.42 | 0.36 |
| As | 0.58 | 0.65 | 0.63 | 0.61 | 0.59 | 0.57 |
| Hydroxyl Value (mgKOH/g) | 18 | 18.1 | 15.5 | 13.3 | 10.7 | 7.9 |
| Molecular weight (Calculated from hydroxyl value) | 3,116 | 3,100 | 3,620 | 4,065 | 5,243 | 7,101 |
| AO addition molecular weight per one functional group | 3,042 | 3,025 | 3,546 | 3,991 | 5,169 | 7,027 |
| Kinematic viscosity (40° C., mm²/s) | 1,116 | 391 | 528 | 1,016 | 3,261 | 10,500 |
| Kinematic viscosity (100° C., mm²/s) | 146 | 55 | 83 | 153 | 388 | 1,025 |
| Unsaturation degree (meq/g) | 0.01 | 0.01 | 0.01 | 0.01 | 0.01 | 0.01 |

TABLE 2

|  | Synthetic Example 7 | Synthetic Example 8 | Synthetic Example 9 | Synthetic Example 10 | Synthetic Example 11 | Comparative Synthetic Example 11 | PREMINOL S 1004F | PREMINOL S 4013F |
|---|---|---|---|---|---|---|---|---|
| $M_L/M_H$ | 0.65 | 0.6 | 0.65 | 0.64 | 0.62 | 3.83 | 1.05 | 0.88 |
| As | 0.65 | 0.6 | 0.66 | 0.64 | 0.61 | 3.93 | 0.97 | 0.83 |
| Hydroxyl value (mgKOH/g) | 28 | 15 | 38.8 | 29 | 17.9 | 17.4 | 17.3 | 10 |
| Molecular weight (Calculated from hydroxyl value) | 4,000 | 7,480 | 4,338 | 5,800 | 9,402 | 3,224 | 3,242 | 11,220 |
| AO addition molecular weight per one functional group | 4,000 | 3,740 | 1,446 | 1,933 | 3,134 | 3,150 | 3,168 | 3,715 |
| Kinematic viscosity (40° C., mm²/s) | 470 | 5,608 | 499 | 856 | 7,500 | 650 | 286 | 3,280 |
| Kinematic viscosity (100° C., mm²/s) | 70 | 606 | 70 | 120 | 815 | 110 | 47 | 453 |
| Unsaturation degree (meq/g) | 0.01 | 0.01 | 0.01 | 0.01 | 0.01 | 0.38 | 0.01 | 0.01 |

Inventive Examples 1 to 11 and Comparative Examples 1 to 3

Hair treatments were prepared according to compositions shown in tables 3 and 4 and the following production method. It was evaluated and judged "slippery feel in rinsing", "slippery feel after rinsing and during removal of water", "smoothness of hairs after drying" and "absence of sticky feel" according to the following standards for judging. The results were also shown in tables 3 and 4. Further, in tables 3 and 4, "NAA-48" (supplied by NOF corporation) was used as cetearyl alcohol and "Cation VB-M flake (supplied by NOF corporation) was used as behentrimonium chloride.

(Production Method)

(1) The components (1) and (2) are heated at 80° C. and uniformly mixed.

(2) (1) is thrown into the component (3), which is emulsified and mixed, followed by cooling to 30° C. or lower while stirring.

(3) Each of the components (4) to (12) is thrown into (2), which is then agitated to be uniform to obtain each hair treatment.

(Evaluation Method)

The four items of "hair slippery feel in rinsing", "hair slippery feel in removing water from hairs after rinsing", "smoothness of hairs after drying" and "Absence of sticky feel" were evaluated by expert panel including 10 females aged 25 to 55 in five grades, according to the following standards. The grades were then summed for the judging.

(Standards)

Evaluation points:

Five points: very good: Four points: good: Three points: Normal

Two points; not so good: One point: Not good

TABLE 3

| No. | Components | Ex. 1 | Ex. 2 | Ex. 3 | Ex. 4 | Ex. 5 | Ex. 6 | Ex. 7 | Ex. 8 |
|---|---|---|---|---|---|---|---|---|---|
| 1 | Cetearyl alcohol | 5.0 | 5.0 | 5.0 | 5.0 | 5.0 | 5.0 | 5.0 | 5.0 |
| 2 | behentrimonium chloride | 2.0 | 2.0 | 2.0 | 2.0 | 2.0 | 2.0 | 2.0 | 2.0 |
| 3 | water | 93.0 | 93.0 | 93.0 | 93.0 | 93.0 | 93.0 | 93.0 | 93.0 |
| 4 | Synthetic example 1 | 5.0 | — | — | — | — | — | — | — |

TABLE 3-continued

| No. | Components | Ex. 1 | Ex. 2 | Ex. 3 | Ex. 4 | Ex. 5 | Ex. 6 | Ex. 7 | Ex. 8 |
|---|---|---|---|---|---|---|---|---|---|
| 5 | Synthetic example 2 | — | 5.0 | — | — | — | — | — | — |
| 6 | Synthetic example 3 | — | — | 5.0 | — | — | — | — | — |
| 7 | Synthetic example 4 | — | — | — | 5.0 | — | — | — | — |
| 8 | Synthetic example 5 | — | — | — | — | 5.0 | — | — | — |
| 9 | Synthetic example 6 | — | — | — | — | — | 5.0 | — | — |
| 10 | Synthetic example 7 | — | — | — | — | — | — | 5.0 | — |
| 11 | Synthetic example 8 | — | — | — | — | — | — | — | 5.0 |
|  | $M_L/M_H$ in GPC chart | 0.52 | 0.62 | 0.58 | 0.52 | 0.42 | 0.37 | 0.65 | 0.6 |
|  | As in GPC chart | 0.58 | 0.65 | 0.63 | 0.61 | 0.59 | 0.57 | 0.65 | 0.6 |
|  | Slippery feel during rinsing | 48 | 46 | 47 | 48 | 49 | 48 | 44 | 46 |
|  | Slippery feel after rinsing and in removing water from hairs | 43 | 45 | 46 | 46 | 48 | 45 | 39 | 45 |
|  | Smoothness of hair after drying | 41 | 43 | 44 | 45 | 46 | 45 | 42 | 42 |
|  | Absence of sticky feel | 41 | 42 | 41 | 40 | 42 | 38 | 42 | 40 |

TABLE 4

| No. | Components | Example 9 | Example 10 | Example 11 | Com. Ex. 1 | Com. Ex. 2 | Com. Ex. 3 |
|---|---|---|---|---|---|---|---|
| 1 | Cetearyl alcohol | 5.0 | 5.0 | 5.0 | 5.0 | 5.0 | 5.0 |
| 2 | Behentrimonium chloride | 2.0 | 2.0 | 2.0 | 2.0 | 2.0 | 2.0 |
| 3 | Water | 93.0 | 93.0 | 93.0 | 93.0 | 93.0 | 93.0 |
| 12 | Synthetic example 9 | 5.0 | — | — | — | — | — |
| 13 | Synthetic example 10 | — | 5.0 | — | — | — | — |
| 14 | Synthetic example 11 | — | — | 5.0 | — | — | — |
| 15 | Comparative Example 1 | — | — | — | 5.0 | — | — |
| 16 | PREMINOL S1004F | — | — | — | — | 5.0 | — |
| 17 | PREMINOL S4013F | — | — | — | — | — | 5.0 |
|  | $M_L/M_H$ in GPC chart | 0.65 | 0.64 | 0.62 | 3.93 | 0.88 | 0.82 |
|  | As in GPC chart | 0.66 | 0.64 | 0.61 | 3.83 | 1.05 | 0.88 |
|  | Slippery feel during rinsing | 44 | 45 | 46 | 43 | 35 | 37 |
|  | Slippery feel after rinsing and in removing water from hairs | 38 | 39 | 43 | 29 | 28 | 30 |
|  | Smoothness of hair after drying | 41 | 42 | 43 | 45 | 42 | 41 |
|  | Absence of sticky feel | 41 | 40 | 39 | 30 | 35 | 27 |

The hair cosmetic containing the alkyloxirane derivative of the present invention having the particular molecular weight distribution does not leave sticky feel or stiff feel, and is excellent in slippery feel in rinsing, and slippery feel during rinsing and during removal of water after the rinsing.

According to the comparative example 1, it was blended the alkyloxirane derivative whose molecular weight distribution was wider in lower molecular weight side. The slippery feel during the removal of water after the rinsing was thus deteriorated and sticky feel was observed.

According to the comparative examples 2 and 3, it was blended the alkyloxirane derivative having very narrow molecular weight distribution. The slippery feel during the rinsing and during removal of water after the rinsing were thus deteriorated and sticky feel was observed.

Experiment B: Hydraulic Oil Composition

Synthesis of Ester Compound

Synthetic Example 1

Into a 5-liter four-necked flask equipped with a thermometer, tube for introducing nitrogen gas, agitator and air-cooling tube, 748 g (5.58 mol) of trimethylolpropane, 1512 g (10.5 mol) of "NAA-82" (Caprylic acid for industrial use having a content of caprylic acid of 99% supplied by NOF corporation) and 1237 g (7.18 mol) of "NAA-102" (Capric acid for industrial use having a content of capric acid of 99%) were charged. The reaction was continued at ambient pressure at 240° C. under nitrogen gas flow while water generated by the reaction was evaporated. Purification by distillation was performed after the reaction to obtain an ester I.

Synthetic Example 2

Into a 5-liter four-necked flask equipped with a thermometer, tube for introducing nitrogen gas, agitator and air-cooling tube, 640 g (4.70 mol) f pentaerythritol, 1121 g (7.77 mol) of "NAA-82" (Caprylic acid for industrial use having a content of caprylic acid of 99% supplied by NOF corporation), 233 g (1.35 mol) of "NAA-102" (Capric acid for industrial use having a content of capric acid of 99% supplied by NOF corporation) and 1483 g (10.3 mol) of 2-ethylhexanoic acid were charged. The reaction was performed under nitrogen gas flow at 240° C. under ambient pressure while water generated by the reaction was removed. Purification by distillation was performed after the reaction to obtain an ester II.

(Synthesis of Alkyloxirane Derivatives)

Each of the alkyloxirane derivatives of the inventive example 1 and comparative example 1 indicated in tables 1 and 2 was synthesized to provide the alkyloxirane derivatives I and II.

(Production of Lubricating Oil Composition)

As the ester compounds obtained above, additives were blended according to the following procedure to prepare lubricating oil compositions of the inventive examples 1 to 3 and comparative examples 2 to 4. The ester I alone was used in the comparative example 1, and ester II alone was used in the comparative example 5.

In a 5-liter four-necked flask equipped with a thermometer, tube for introducing nitrogen, agitator and Dimroth condenser, the ester compound and alkyloxirane derivative synthesized as described above were mixed and agitated at room temperature for 1 hour in a blending ratio indicated in table 5, to obtain hydraulic oil composition.

As to the hydraulic oil compositions, the viscosity test. rubber immersion test and lubricating performance test (SRV test) were performed according the methods as described below, and the results were described in table 5.
(Viscosity)

Viscosity was measured according to Japan Industrial Standards JIS K 2283.
(Rubber Immersion Test)

The temperature of each of the lubricating oil compositions was set at 80° C., and each test piece (20.0×30.0×2.0 mm) of butyl rubber was immersed in the composition for 14 days (336 hours). It was measured a ratio of weight change before and after the immersion.

It was calculated the effect of preventing swelling with respect to that in the comparative example 1, based on the value of the ratio of the weight change. As the value of the effect of preventing swelling is higher, the compatibility to a sealant is better. "⊚" is assigned to the value of 50% or higher, "○" is assigned to 10% or higher and below 50%, and "x" is assigned to below 10%.

Effect of preventing swelling (%)=(1−"ratio of weight change of each test piece"/"ratio of weight change of comparative example 1")×100

Case of Inventive Example 1

Effect of preventing swelling (%)=(1−"ratio of weight change of inventive example 1"/"ratio of weight change of comparative example 1")×100

(Lubricating Performance Test (SRV Test))

The test was performed in ball-on disk setting, and each test piece was made of SUJ-2. The test was performed under conditions of a test temperature of 40° C., a load of 100N, an amplitude of 1 mm and a frequency of 50 Hz. The scar diameter (μm) after 25 minutes of the test time was measured. As the scar diameter is smaller, the lubricating performance is better.

As can be seen from the results shown in table 5, the ester I of the comparative example 1 is inferior in the compatibility to a sealant and lubricating performance (wear resistance), as the alkyloxirane derivative is not blended.

In each of the hydraulic oil compositions of the comparative examples 2 to 4, the values of $M_L/M_H$ and As of the alkyloxirane derivative II is high, and it is blended the alkyloxirane derivative whose molecular weight distribution is wider in the lower molecular weight side. The lubricating property is thus deteriorated. Further, the compatibility to s sealant is also deteriorated compared with the case that the same amount of the alkyloxirane derivative I is blended.

According to the comparative example 5, the ester II is used and alkyloxirane derivative is not blended. Thus, although the value of the kinematic viscosity is comparable with that in the inventive example 3, the lubricating property (wear resistance) is deteriorated and the compatibility to a sealant is also inferior.

Experiment C: Active Energy Ray-Curable Resin Composition

Synthetic Examples 1 and 2: Synthesis of Alkyloxirane Derivatives (a1-1) and (a1-2)

Each of alkyloxirane derivatives of synthetic examples 7 and 8 shown in table 2 were synthesized, and it was assigned the alkyloxirane derivatives (a1-1) and (a1-2), respectively.

Comparative Synthetic Example 1: Synthesis of Alkyloxirane Derivative (a'1-1)

Into a 5-liter (inner volume of 4890 ml) of a stainless pressure-proof reaction bath equipped with a thermometer, pressure gauge, security valve, tube for blowing nitrogen gas, agitator, vacuum discharge tube, cooling coil and vacuum jacket, 84 g of propylene glycol and 10.8 g of potassium hydroxide were charged. 2588 g of propylene oxide was reacted at 100° C., the residual propylene oxide was removed under reduced pressure at 0° C. for 30 minutes, the reaction product was moved into a 5-liter eggplant flask

TABLE 5

| | Example 1 | Example 2 | Example 3 | Com. Ex. 1 | Com. Ex. 2 | Com. Ex. 3 | Com. Ex. 4 | Com. Ex. 5 |
|---|---|---|---|---|---|---|---|---|
| Ester I | 100 | 100 | 100 | 100 | 100 | 100 | 100 | — |
| Ester II | — | — | — | — | — | — | — | 100 |
| Alkyloxirane derivative I | 5 | 10 | 20 | — | — | — | — | — |
| Alkyloxirane derivative II | — | — | — | — | 5 | 10 | 20 | — |
| Kinematic viscosity(40° C., mm2/s) | 22.39 | 25.75 | 34.62 | 19.57 | 22.1 | 25.06 | 32.68 | 33.32 |
| Kinematic viscosity(100° C., mm2/s) | 4.87 | 5.45 | 6.94 | 4.374 | 4.84 | 5.39 | 6.76 | 5.764 |
| Swelling ratio | 29.9 | 25.1 | 16.4 | 34.1 | 30.9 | 27.1 | 18.7 | 31.9 |
| Suppression effect With respect to Com. Ex. 1 | ○ | ○ | ⊚ | — | X | ○ | ○ | — |
| Lubricating property (Scar diameter: μm) | 390 | 380 | 390 | 640 | 530 | 550 | 520 | 590 |

As can be seen from the results shown in table 5, each of the hydraulic oil compositions of the inventive examples 1 to 3, obtained by blending the alkyloxirane derivative having the specific molecular weight distribution to the specific ester of the invention, is excellent in the compatibility to a sealant and lubricating performance (wear resistance).

and promptly neutralized by 1N hydrochloric acid, followed by removal of water under nitrogen gas atmosphere and filtration, to obtain a compound (a'1-1)

The thus obtained reaction product (a'1-1) was subjected to measurement by means of gel permeation chromatography. As a result, $M_L/M_H$ was probed to be 1.25.

Synthetic Example 3: Synthesis of Urethane Compound (A-1)

326 g of (a1-1) and 0.05 g of dibutyl tin dilaurate were charged into a flask equipped with an agitator, tube for supplying gas, cooling tube and thermometer, and the temperature was elevated to 40° C. Then, 6.8 g of hexamethylene diisocyanate (Duranate 50M-HDI supplied by ASAHIKASEI CHEMICALS. CORPORATION; referred to as "HDI" below) as (a2) was added dropwise over 2 hours noting the heat generation. After the termination of dropping, the reaction was performed at 60° C. for 2 hours until the content of isocyanate group is less than 0.1% or lower according to the method described in JIS K 7301, so that the urethane compound (A-1) was obtained.

Synthetic Example 4: Synthesis of Urethane Compound (A-2)

The urethane compound (A-2) was obtained according to the same synthetic method as that of the synthetic example 3.

Synthetic Example 5: Synthesis of Urethane Compound (A'-1)

319 g of (a'1-1) and 0.05 g of dibutyl tin dilaurate were charged in a flask equipped with an agitator, tube for supplying gas, cooling tube and thermometer, and the temperature was raised to 40° C. Then, 13.4 g of HDI as (a2) was added dropwise over 2 hours noting heat generation. After the termination of the dropping, the reaction was performed at 60° C. for 2 hours until the content of isocyanate group is lower than 0.1 percent or lower according to the method described in JIS K 7301, so that the urethane compound (A'-1) was obtained.

Synthetic Example 6: Synthesis of Urethane (Meth) Acrylate (B-1)

Into a flask equipped with an agitator, tube for supplying gas, cooling tube and thermometer, it was charged 258 g of mixture of pentaerythritol triacrylate and pentaerythritol tetraacrylate ("Viscoat 300" supplied by Osaka Organic Chemical Industry Ltd.; hydroxyl value; 130 mg KOH/g, pentaerythritol triacrylate/pentaerythritol tetraacrylate is 70/30 (mass %)), 0.05 g of hydroquinone monomethyl ether and 0.05 g of dibutyl tin dilaurate, followed by the temperature elevation to 40° C. while air is blown. 50.5 g of HDI was then added dropwise over 2 hours noting heat generation. After the termination of the dropping, the reaction was performed at 60° C. for 2 hours until the content of isocyanate group is below 0.1% according to the method described in JIS K 7301. It was thus obtained mixture of 6-functional urethane acrylate (B-1, number average molecular weight of 765)/pentaerythritol tetraacrylate (mixture of mass ratio of 75/25).

Synthetic Example 7: Synthesis of Urethane (Meth)Acrylate (B-2)

It was obtained mixture of 9-functional urethane acrylate (B-2) (number average molecular weight is 1398)/pentaerythritol tetraacrylate (mixture of 78/22 in mass ratio), according to the same method as the synthetic example 6.

TABLE 6

| | (a1) or (a'1) | | (a2) |
|---|---|---|---|
| | Z | n | |
| A-1 | Polyoxypropylene glycol (Molecular weight 700) | 57 | Hexamethylene diisocyanate |
| A-2 | Polyoxypropylene glycol (Molecular weight 700) | 117 | Isophoron diisocyanate |
| A'-1 | Propylene glycol | 33 | Hexamethylene diisocyanate |
| B-1 | Pentaerythritol triacrylate./pentaerythritol tetraacrylate = 70/30 (mass %) | | Hexamethylene diisocyanate |
| B-2 | Pentaerythritol triacrylate./pentaerythritol tetraacrylate = 70/30 (mass %) | | Isocyanurate product of hexamethylene diisocyanate |

Inventive Example 1

1.0 g of urethane compound (A-1) obtained in the synthetic example 3 and 9.0 g of urethane (meth)acrylate (B-1) were weighed in a 30 ml brown screw tube, and 0.3 g of 1-hydroxycyclohexyl phenyl tone (Irgacure 184 supplied by BASF corporation) as a photo initiator was weighed. These were mixed in a vortex mixer for 1 minute to obtain active energy ray-curable resin composition. The thus obtained active energy ray-curable resin composition was applied on a predetermined substrate in a dry film thickness of 25p m. 80 W/cm of non-electrode UV lamp (H valve) was used to irradiate light of an energy amount of integrated quantity of light of 500 mJ/cm$^2$ to obtain a test piece of the cured product. The test piece of the cured product was used to perform the following evaluation.

(Transparency)

As to the test piece of the cured film product with a substrate of a polycarbonate plate (supplied by Nippon Test Panel Co., Ltd, thickness of 1 mm, 70×150 mm), the total light transmittance (%) was evaluated based on JIS K7361 and the following standards.

Total light transmittance is 92% or higher (evaluation "⊚")

Total light transmittance is 90% or higher (evaluation "○")

Total light transmittance is below 90% (evaluation "x")

(Surface Hardness)

As to the test piece of the cured film product with a substrate of a polycarbonate plate (supplied by Nippon Test Panel Co., Ltd, thickness of 1 mm, 70×150 mm), scratch hardness was measured based on JIS K5600 at a load of 750 g (pencil hardness test) and evaluated based on the following standards.

Pencil hardness is 2 H or higher (evaluation "⊚")

Pencil hardness is F to H (evaluation "○")

Pencil hardness is 2 B or lower (evaluation "x")

(Resistance Against Impact)

As to the test piece of the cured film product with a substrate of a glass plate (supplied by Matsunami Glass Co. Ltd., thickness of 1 mm, 40×75 mm), a steel ball (diameter of 16 mm and weight of 16 g) was dropped under conditions of 251 and 60 RH %. It was judged the maximum height according to the following standards, in which scars are not observed on the surface of the cured film and cracks were not observed in the glass substrate.

"⊚": The maximum height is 45 cm or larger.
"○": The maximum height is 35 to 44 nm.
"x": The maximum height is 34 cm or smaller.

Inventive Examples 2 and 3: Comparative Example 1 and 2

Each of active energy ray-curable resin compositions was prepared in a blending ratio described in table 7, and subjected to the evaluation same as that in the inventive example 1. The results of the evaluation were shown in table 7.

TABLE 7

|  |  |  | Example 1 | Example 2 | Example 3 | Com. Ex. 1 | Com. Ex. 2 |
|---|---|---|---|---|---|---|---|
| Blending ratio | Component (A) | A-1 | 1.0 |  | 3.0 |  |  |
|  |  | A-2 |  | 2.0 |  |  |  |
|  | Component (A') | A'-1 |  |  |  |  | 1.0 |
|  | Component (B) | B-1 | 9.0 | 8.0 |  | 10 | 9.0 |
|  |  | B-2 |  |  | 7.0 |  |  |
|  | Photo initiator | Irgacure 184 | 0.3 | 0.3 | 0.3 | 0.3 | 0.3 |
|  |  | Total | 10.3 | 10.3 | 10.3 | 10.3 | 10.3 |
| Blending | (A)/(B) |  | 10/90 | 20/80 | 30/70 | 0/100 | 10/90 |
|  | $M_L/M_H$ |  | 0.65 | 0.6 | 0.65 | — | 1.25 |
| Evaluation results | Transparency |  | ⊚ | ⊚ | ⊚ | ⊚ | ⊚ |
|  | Surface hardness |  | 3H | 2H | 3H | 3H | 2H |
|  | Resistance against impact |  | ⊚ | ⊚ | ○ | X | X |

As can be seen from the results of evaluation shown in table 7, each of the active energy ray-curable resin compositions of the inventive examples 1 to 3 provides a cured product excellent in transparency, surface hardness and resistance against impact.

According to the comparative example 1 shown in table 7 without the component (A), although the transparency and surface hardness were excellent, the resistance against impact was inferior. Further, according to the comparative example 2, $M_L/M_H$ calculated from the GPC chart of the component (A) is out of the range of the present invention, and the resistance against impact was proved to be inferior.

Experiment D: Oil Cleansing Agent

Each of the alkyloxirane derivatives of the synthetic examples 4, 5 and 6 shown in table 1 was synthesized, and used as compounds A-1 to A-3 used in the inventive examples 1 to 8 and comparative examples 1 to 5.

Tables 1 and 2 show the values of $M_L/M_H$ and As calculated from chromatograms and the properties of the compounds A-1 to A-3", PREMINOL S1004F" (supplied by AGC Inc., high molecular weight·low by-product polyether polyol, number of functional groups is 1) and "PREMINOL S4013F" (supplied by AGC Inc., high molecular weight·low by-product polyether polyol, number of functional groups is 2) as the component (a').

Inventive Examples 1 to 8 and Comparative Examples 1 to 5

As shown in tables 8 and 9, oil cleansing agents were prepared, and "elongation at the initial application", "slippery feel in use", "cleansing effect", "rinsing property" and "moisture feel after washing" were evaluated and judged based on the following judging standards.

(1) Spreading at Initial Application

The feel at initiation of application of cleansing agents was evaluated to give evaluation points as follows by panelists composed of 10 females (aged 22 to 37) performing make-up. Then a total of the evaluation points was used to give evaluation of the following four grades of "⊚" to "x".

Two points: In the case that spreading at the initial application is good and feels light.

One point: In the case that spreading at the initial application is not so good and feels heavy to some extent.

Zero point: In the case that spreading at the initial application is not good and feels heavy.

(Evaluation by 5 grades based on a total of the evaluation points)

"⊚": Total of evaluation points is 18 points or higher.
"○": Total of evaluation points is 15 points or higher and below 17 points.
"Δ": Total of evaluation points is 10 points or higher and below 14 points.
"x": Total of evaluation points is below 10 points.

(2) Smoothness in Use

Feeling (in use) during the time of blending the cleansing agent with makeup was evaluated as follows to give evaluation points, by panelists composed of 10 females (aged 22 to 37) with make-up. Then, the following evaluation of 4 grades of "⊚" to "x" was given based on a total of the evaluation points.

Two points: In the case that smoothness in use is good and feels light.

One point: In the case that smoothness in use is not so good and feels heavy to some extent.

Zero point: In the case that smoothness in use is bad and feels heavy.

(Evaluation by 5 grades based on a total of the evaluation points)

"⊚": Total of evaluation points is 18 points or higher.
"○": Total of evaluation points is 15 points or higher and below 17 points.
"Δ": Total of evaluation points is 10 points or higher and below 14 points,
"x": Total of evaluation points is below 10 points.

(3) Cleansing Effect

The blending of the cleansing agent with make-up was evaluated to give evaluation points, by panelists composed of 10 females aged 22 to 37 with make-up. Then, the following four-grade evaluation of "⊚" to "x" was performed based a total of the evaluation points.

Two points: In the case that make-up is sufficiently removed

One point: In the case that feel of removal of make-up is not so good

Zero point: In the case that removal of make-up is clearly not good (Evaluation by 5 Grades Based on a Total of the Evaluation Points)

"⊚": Total of evaluation points is 18 points or higher.

"○": Total of evaluation points is 15 points or higher and below 17 points.

"Δ": Total of evaluation points is 10 points or higher and below 14 points.

"X": Total of evaluation points is below 10 points.

(4) Rinsing Property

The rinsing property in rinsing with cool water (15° C.) after using the cleansing agent was evaluated to give evaluation points, by panelists composed of 10 females (aged 22 to 37) with make-up. Then, the following evaluation of 4 grades of "⊚" to "x" was given based on a total of the evaluation points.

Two points: In the case of feeling that rinsing is promptly completed without slime during the rinsing.

One point: In the case of feeling that some slime is left after the rinsing and the rinsing property is not so good.

Zero point: Slime is difficult to remove and the rinsing property is clearly bad.

(Evaluation by 5 grades based on a total of the evaluation points)

"⊚": Total of evaluation points is 18 points or higher.

"○": Total of evaluation points is 15 points or higher and below 17 points.

"Δ"; Total of evaluation points is 10 points or higher and below 14 points.

"x": Total of evaluation points is below 10 points.

(5) Moistness of Skin after Washing

The moistness of skin was evaluated to give evaluation points as follows, after the rinsing was performed in warm water (40° C.) with the cleaning agent, followed by standing for 10 minutes in a room having a humidity of 30% (dry condition in winter), by panelists composed of 10 females (aged 22 to 37) with make-up. Then, the following evaluation of 4 grades of "⊚" to "x" was given based on a total of the evaluation points.

Two points: In the case of feeling that skin is humidified and moisturized.

One point: In the case of feeling that skin is not so moisturized and dry to some extent.

Zero point: in the case of feeling that skin is dry and feels rough when touching.

(Evaluation by 5 grades based on a total of the evaluation points)

"⊚": Total of evaluation points is 18 points or higher.

"○": Total of evaluation points is 15 points or higher and below 17 points.

"Δ": Total of evaluation points is 10 points or higher and below 14 points.

"x": Total of evaluation points is below 10 points.

TABLE 8

| | | Inventive examples | | | | | | | |
|---|---|---|---|---|---|---|---|---|---|
| | Components | 1 | 2 | 3 | 4 | 5 | 6 | 7 | 8 |
| a | Compound A-1 | 3.0 | | | | | | | 1.5 |
| | Compound A-2 | | 3.0 | | 14.0 | 3.0 | 3.0 | 10.0 | |
| | Compound A-3 | | | 3.0 | | | | | 1.5 |
| b | Olive oil | 42.0 | 42.0 | 42.0 | 37.0 | 53.3 | 32.6 | 43.9 | 42.0 |
| | Ethyl hexyl palmitate | 25.0 | 25.0 | 25.0 | 22.0 | 31.7 | 19.4 | 26.1 | 25.0 |
| | Total of mass of component (b) | 67.0 | 67.0 | 67.0 | 55.0 | 85.0 | 52.0 | 70.0 | 67.0 |
| c | Sorbitan monooleate (HLB = 4.3) | 5.0 | 5.0 | 5.0 | 4.0 | 2.0 | 7.5 | 3.3 | 5.0 |
| | Polyoxyethylene sorbit tetraoleate(HLB = 11.5) | 25.0 | 25.0 | 25.0 | 22.0 | 10.0 | 37.5 | 16.7 | 25.0 |
| | Total of mass of component (c) | 30.0 | 30.0 | 30.0 | 31.0 | 12.0 | 45.0 | 20.0 | 30.0 |
| | Total | | | | 100.0 | | | | |
| Evaluation results | Elongation at initial application | ⊚ (18) | ⊚ (18) | ○ (16) | ○ (15) | ⊚ (19) | ○ (15) | ⊚ (18) | ○ (17) |
| | Slippery feel in use | ⊚ (20) | ⊚ (20) | ⊚ (20) | ○ (17) | ⊚ (20) | ⊚ (18) | ○ (17) | ○ (17) |
| | Cleansing effect | ⊚ (19) | ⊚ (19) | ⊚ (19) | ⊚ (19) | ⊚ (19) | ⊚ (19) | ⊚ (19) | ⊚ (19) |
| | Rinsing property | ⊚ (20) | ⊚ (20) | ⊚ (20) | ⊚ (20) | ○ (15) | ⊚ (20) | ○ (17) | ⊚ (18) |
| | Moisture feel of skin after washing | ○ (17) | ⊚ (19) | ⊚ (19) | ⊚ (20) | ⊚ (19) | ○ (15) | ⊚ (20) | ⊚ (19) |

TABLE 9

| | | Comparative Examples | | | | |
|---|---|---|---|---|---|---|
| | Components | 1 | 2 | 3 | 4 | 5 |
| a | Compound A-1 | | | | | |
| | Compound A-2 | | | | 10.0 | 30.0 |
| | Compound A-3 | | | | | |
| a' | PREMINOL S1004F | 3.0 | | | | |
| | PREMINOL S4013F | | 3.0 | | | |

TABLE 9-continued

|   | Components | Comparative Examples 1 | 2 | 3 | 4 | 5 |
|---|---|---|---|---|---|---|
| b | Olive oil | 42.0 | 42.0 | 56.4 | 25.1 | 28.2 |
|   | Ethyl hexyl palmitate | 25.0 | 25.0 | 33.6 | 14.9 | 16.8 |
|   | Total of mass of component (b) | 67.0 | 67.0 | 80.0 | 40.0 | 45.0 |
| c | Sorbitan monooleate (HLB = 4.3) | 5.0 | 5.0 | 3.3 | 8.3 | 0.8 |
|   | Polyoxyethylene sorbit tetraoleate (HLB = 11.5) | 25.0 | 25.0 | 16.7 | 41.7 | 4.2 |
|   | Total of mass of component (c) | 30.0 | 30.0 | 20.0 | 50.0 | 5.0 |
| Evaluation items | Total Elongation at initial application | X (8) | X (9) | ○ (16) | X (9) | X (7) |
|   | Slippery feel in use | X (8) | X (9) | X (9) | ○ (15) | Δ (13) |
|   | Cleansing effect | ⊚ (19) | ⊚ (19) | ⊚ (19) | X (9) | X (9) |
|   | Rinsing property | ○ (17) | ○ (17) | ○ (16) | ⊚ (18) | X (9) |
|   | Moisture feel of akin after washing | X (8) | X (9) | X (8) | Δ (12) | Δ (10) |

As can be seen from the inventive examples 1 to 8, the oil cleansing agent containing the component of the present invention was excellent in the elongation at the initial application, slippery feel in use, cleansing effect, rinsing property and moisture feel of skin after the washing.

On the other hand, the comparative examples 1 to 5 did not provide sufficiently high performances.

According to the comparative examples 1 and 2, it is blended the alkyloxirane derivative having a narrow range of distribution of molecular weight instead of the component (a). The elongation at the initial application, slippery feel in use and moisture feel of skin after washing were insufficient.

According to the comparative example 3, the component (a) is not contained. The slippery feel in use and moisture feel of skin after washing were thus insufficient.

According to the comparative example 4, the content of the component (b) is low. The elongation at the initial application and cleansing performance were thus insufficient.

According to the comparative example 5, the content of the component (a) is high. The elongation at the initial application, slippery feel in use, cleansing performance and rinsing property were thus insufficient.

The invention claimed is:

1. An alkyloxirane derivative represented by formula (1) below, wherein $M_H$ and $M_L$ calculated from a chromatogram obtained by gel permeation chromatography measurement of said alkyloxirane derivative satisfy formula (2) below:

$$Z-[O-(AO)n-H]x \quad (1)$$

in the formula (1),

Z represents a residual group of a compound having a carbon number of 1 to 22 and one to six hydroxyl groups wherein all of said hydroxyl groups are excluded from said compound, x represents a number of 1 to 6, AO represents an oxyalkylene group having a carbon number of 3 and n represents a number of 25 or more;

$$0.35 \leq M_L/M_H \leq 0.75 \quad (2)$$

provided that L is assigned to a length of a perpendicular line from the maximum point K at which an intensity of a refractive index on said chromatogram takes the maximum value to a base line B, provided that points O and Q are assigned to two points at which said intensity of said refractive index on said chromatogram is L/2, said point O has a shorter elution time and said point Q has a longer elution time, and provided that P is assigned to an intersecting point where a straight line G connecting said point O and point Q intersects said perpendicular line from said maximum point K to said base line, $M_H$ represents a distance between said point O and said intersecting point P, and $M_L$ represents a distance between said point Q and said intersecting point P, wherein the alkyloxirane derivative is produced by ring-opening addition polymerization of methyloxirane, wherein the average supply rates of methyloxirane to the reaction mixture are controlled as follows:

$$V_1/V_2 = 1.1 \text{ to } 2.0$$

$$V_2/V_3 = 1.1 \text{ to } 1.5$$

where $V_1$ represents a rate (supply amount per an unit time) when between 5 to 20 wt % of a total supply amount of methyloxirane is supplied, $V_2$ represents a rate when between 20 to 50 wt % of a total supply amount of methyloxirane is supplied, and $V_3$ represents a rate when between 50 to 100 wt % of a total supply amount of methyloxirane is supplied.

2. The alkyloxirane derivative of claim 1, wherein As calculated from said chromatogram satisfies the following formulas (3) and (4):

$$As = W_{1/2}/W_{5\%} \quad (3)$$

$$0.30 \leq As \leq 0.70 \quad (4)$$

provided that points S and R are assigned to two points at which said intensity of said refractive index on said chromatogram is L/20, said point R has a shorter elution time and said point S has a longer elution time, and provided that T is assigned to an intersecting point where a straight line H connecting said point R and point S intersects said perpendicular line from said maximum point K to said base line B, $W_{1/2}$ is assigned to a distance between said point R and said intersecting point T, and $W_{5\%}$ is assigned to a distance between said point R and said point S.

3. The alkyloxirane derivative of claim 1, wherein said alkyloxirane derivative is represented by the following formula (5):

$$R^1O\text{-}(AO)n\text{-}H \tag{5}$$

$R^1$ represents a hydrocarbon group having a carbon number of 1 to 22;

AO represents said oxyalkylene group having a carbon number of 3: and n represents said number of 25 or more.

4. A hair cosmetic composition comprising said alkyloxirane derivative of claim 1.

5. A hydraulic oil composition comprising:
   an ester compound (A) as follows; and
   said alkyloxirane derivative (B) of claim 1,
   wherein 1.0 to 30.0 mass parts of said alkyloxirane derivative (B) is contained with respect to 100 mass parts of said ester compound (A):
   (A) said ester compound of neopentyl polyol having a carbon number of 5 to 10 and an alcohol valence of 3 to 6 and of a fatty acid having a carbon number of 6 to 22.

6. An active energy ray-curable resin composition comprising the following component (A) and component (B), wherein a ratio of a mass of said component (A) with respect to a mass of said component (B) ((A)/(B)) is 1/99 to 30/70,
   said component (A):
   an urethane compound of a reaction product of said alkyloxirane compound (a1) of claim 1 and of an isocyanate (a2) comprising two or more isocyanate groups in a molecule of said isocyanate;
   said component (B):
   an urethane (meth)acrylate compound having two or more ethylenically unsaturated groups.

7. An oil cleansing agent comprising:
   1 to 20 mass % of a component (a) below;
   45 to 90 mass % of a component (b) below; and
   5 to 50 mass % of a component (c) below:
   (a) said alkyloxirane compound of claim 2;
   (b) a liquid oily component; and
   (c) a surfactant of an ester of a polyvalent alcohol and a fatty acid.

* * * * *